(12) United States Patent
Bezzerides et al.

(10) Patent No.: US 9,603,559 B2
(45) Date of Patent: Mar. 28, 2017

(54) CAPILLARY REFILL TIME DIAGNOSTIC APPARATUS AND METHODS

(75) Inventors: Vassilios Bezzerides, Brookline, MA (US); Mark Ian Neuman, Wayland, MA (US)

(73) Assignee: Children's Medical Center Corporation, Boston, MA (US)

( * ) Notice: Subject to any disclaimer, the term of this patent is extended or adjusted under 35 U.S.C. 154(b) by 1272 days.

(21) Appl. No.: 13/518,452

(22) PCT Filed: Dec. 23, 2010

(86) PCT No.: PCT/US2010/003244
§ 371 (c)(1),
(2), (4) Date: Sep. 27, 2012

(87) PCT Pub. No.: WO2011/078882
PCT Pub. Date: Jun. 30, 2011

(65) Prior Publication Data
US 2013/0018241 A1   Jan. 17, 2013
US 2013/0211216 A9   Aug. 15, 2013

Related U.S. Application Data

(60) Provisional application No. 61/290,021, filed on Dec. 24, 2009.

(51) Int. Cl.
*A61B 5/00* (2006.01)
*A61B 5/1455* (2006.01)

(52) U.S. Cl.
CPC ........ *A61B 5/14552* (2013.01); *A61B 5/0053* (2013.01); *A61B 5/0055* (2013.01);
(Continued)

(58) Field of Classification Search
USPC ................................................ 600/324, 479
See application file for complete search history.

(56) References Cited

U.S. PATENT DOCUMENTS

| | | |
|---|---|---|
| 3,698,382 A | 10/1972 | Howell |
| 4,213,462 A | 7/1980 | Sato |

(Continued)

FOREIGN PATENT DOCUMENTS

| | | |
|---|---|---|
| WO | WO 2007/086071 A1 | 8/2007 |
| WO | WO 2007/113756 A1 | 10/2007 |

(Continued)

OTHER PUBLICATIONS

[No Author Listed] Practice parameter: the management of acute gastroenteritis in young children. American Academy of Pediatrics, Provisional Committee on Quality Improvement, Subcommittee on Acute Gastroenteritis. Pediatrics. Mar. 1996;97(3):424-35.

(Continued)

*Primary Examiner* — Michael Kahelin
*Assistant Examiner* — Mitchell E Alter
(74) *Attorney, Agent, or Firm* — Wolf, Greenfield & Sacks, P.C.

(57) ABSTRACT

An apparatus for measuring capillary refill time has a measurement module containing at least two radiation sources and at least one detector configured to detect radiation from each source that interacts with and is received from a measurement region of a patient or subject. One radiation source may be characterized by a wavelength that is absorbed substantially equally by oxyhemoglobin and deoxyhemoglobin. The other radiation source may be substantially unaffected by the presence or absence of blood in the measurement region. The measurement module may be applied against a measurement region of a patient for a first time period, and the released from the measurement region for a second time period, and detected signals processed to quantitatively evaluate capillary refill time.

18 Claims, 10 Drawing Sheets

(52) U.S. Cl.
CPC ............ *A61B 5/412* (2013.01); *A61B 5/6826* (2013.01); *A61B 5/6838* (2013.01); *A61B 5/7239* (2013.01)

(56) References Cited

U.S. PATENT DOCUMENTS

| | | | |
|---|---|---|---|
| 4,494,550 | A | 1/1985 | Blazek et al. |
| 4,723,554 | A | 2/1988 | Oman et al. |
| 5,050,613 | A | 9/1991 | Newman et al. |
| 5,377,674 | A * | 1/1995 | Kuestner ............ A61B 5/14546 356/41 |
| 5,692,503 | A * | 12/1997 | Kuenstner .......... A61B 5/14551 356/41 |
| 5,769,791 | A | 6/1998 | Benaron et al. |
| 5,836,872 | A | 11/1998 | Kenet et al. |
| 5,963,333 | A | 10/1999 | Walowit et al. |
| 6,091,984 | A | 7/2000 | Perelman et al. |
| 6,223,063 | B1 * | 4/2001 | Chaiken ............. A61B 5/02427 600/310 |
| 6,289,230 | B1 | 9/2001 | Chaiken et al. |
| 6,393,310 | B1 * | 5/2002 | Kuenstner ............ A61B 5/0059 600/310 |
| 6,685,635 | B2 | 2/2004 | Shani et al. |
| 7,003,337 | B2 | 2/2006 | Harjunmaa et al. |
| 7,291,109 | B1 | 11/2007 | Sarvazyan |
| 7,483,733 | B2 | 1/2009 | Shani et al. |
| 2002/0165439 | A1 | 11/2002 | Schmitt |
| 2003/0212316 | A1 | 11/2003 | Leiden et al. |
| 2006/0129040 | A1 | 6/2006 | Fine et al. |
| 2007/0282182 | A1 * | 12/2007 | Messerges ........... A61B 5/0059 600/324 |
| 2008/0015449 | A1 | 1/2008 | David |
| 2009/0143655 | A1 | 6/2009 | Shani |

FOREIGN PATENT DOCUMENTS

| | | | |
|---|---|---|---|
| WO | WO 2009/053920 | * | 4/2009 |
| WO | WO 2009/053920 A1 | | 4/2009 |

OTHER PUBLICATIONS

Cagli et al., Correlation of modified alien test with Doppler ultrasonography. Asian Cardiovasc Thorac Ann. Apr. 2006;14(2):105-8.

Gorelick et al., Effect of ambient temperature on capillary refill in healthy children. Pediatrics. Nov. 1993;92(5):699-702.

Gorelick et al., Validity and reliability of clinical signs in the diagnosis of dehydration in children. Pediatrics. May 1997;99(5):E6.

Schriger et al., Defining normal capillary refill: variation with age, sex, and temperature. Ann Emerg Med. Sep. 1988;17(9):932-5.

Shavit et al., A novel imaging technique to measure capillary-refill time: improving diagnostic accuracy for dehydration in young children with gastroenteritis. Pediatrics. Dec. 2006;118(6):2402-8.

Steiner et al., Is this child dehydrated? JAMA. Jun. 9, 2004;291(22):2746-54.

PCT/US2010/003244, Mar. 14, 2011, International Search Report and Written Opinion.

PCT/US2010/003244, Jul. 5, 2012, International Preliminary Report on Patentability.

* cited by examiner

CAPILLARY REFILL TIME DIAGNOSTIC APPARATUS AND METHODS

CROSS-REFERENCE TO RELATED U.S. APPLICATIONS

The present application is a National Stage of International Application Serial No. PCT/US2010/003244, filed Dec. 23, 2010, which claims the benefit of U.S. provisional patent application No. 61/290,021 filed on Dec. 24, 2009, which is incorporated herein by reference.

BACKGROUND

Dehydration is one of the most common conditions encountered in pediatric emergency departments among children less than 18 years of age, accounting for nearly 500,000 visits in the United States annually. Determining dehydration and its severity in infants, children, adolescents, or adults, is a procedure that may be frequently encountered in clinical and acute care settings. In some cases, it is necessary to accurately and quickly assess hydration and perfusion status of a patient so that a plan for patient care can be immediately determined and administered.

Typically, dehydration is evaluated visually and/or manually by a clinician, e.g., measuring blood pressure and heart rate, observing for sunken eyes, pinching a patient's skin to evaluate elasticity, pressing on a capillary bed and releasing to assess a change in coloration as a function of time. For example, a clinician may apply pressure to a fingernail or toenail of the patient until the region under the fingernail or toenail blanches. This indicates that blood has been forced from the capillary bed below the nail. The clinician then releases the pressure and measures the time required for the region to regain its original color. This time is referred to as a capillary refill time. Besides requiring valuable time of a skilled physician, such manual tests only provide qualitative information about a patient's degree of dehydration or vascular functioning.

SUMMARY

Automated devices for measuring capillary refill time have been described; however, the inventors have recognized improvements to such devices. The inventors have conceived and developed improved apparatus and methods that may be used to quantitatively and automatically measure capillary refill time in a patient. The resulting measurement of capillary refill time may be used to determine an extent of dehydration in a patient or evaluate another condition of the patient, e.g., vascular function related to sepsis, heart disease, heart failure, or shock.

According to one embodiment, an apparatus for measuring capillary refill time comprises a first source for emitting first radiation characterized by a first wavelength, a second source for emitting second radiation characterized by a second wavelength, and at least one detector for detecting the first radiation and the second radiation. The apparatus may further comprise a probe including a convex surface configured to be controllably applied against and released from a measurement region, wherein the measurement region includes a capillary bed. According to this embodiment, the first source and second source may be configured to radiate the measurement region and the at least one detector may be configured to detect the first radiation and the second radiation received from the measurement region. The first radiation may be selected to be absorbed substantially equally by an amount of oxyhemoglobin or the same amount of deoxyhemoglobin. The at least one detector may comprise at least one first detector including a first radiation filter, wherein the at least one first detector and first radiation filter are configured to detect substantially only the first radiation received from the measurement region and to provide a first signal representative of the first radiation received from the measurement region. The at least one detector may further comprise at least one second detector including a second radiation filter, wherein the at least one second detector and second radiation filter are configured to detect substantially only the second radiation received from the measurement region and to provide a second signal representative of the second radiation received from the measurement region. The apparatus may include at least one processor, and be configured to calculate a ratio of the first signal and second signal.

It will be appreciated that additional embodiments of an apparatus for measuring capillary refill time may comprise any combination of the elements presented above and additional elements described below. Some elements presented above may be omitted in some embodiments, and some elements described below may be added in some embodiments. For example, some embodiments of the apparatus may include a probe having a convex surface and some embodiments of the apparatus may not include a probe having a convex surface.

One embodiment of the invention includes a method for measuring capillary refill time. The method comprises acts of emitting, by a first source, first radiation characterized by a first wavelength onto a measurement region including a capillary bed, emitting, by a second source, second radiation characterized by a second wavelength onto the measurement region, and detecting, by at least one detector, the first radiation and the second radiation received from the measurement region. The method may further include acts of controllably applying and releasing a convex surface of a probe against the measurement region, and calculating a value representative of a ratio of the first radiation and the second radiation received from the measurement region. The first radiation may be selected based on its being absorbed substantially equally by an amount of oxyhemoglobin or the same amount of deoxyhemoglobin. The method may further comprise acts of modulating any one of or a combination of: the first source, the second source and the at least one detector. The method of measuring capillary refill time may further include acts of emitting the first radiation through at least a transparent portion of the convex surface of the probe, emitting the second radiation through at least a transparent portion of the convex surface; and detecting the first radiation and/or the second radiation through at least a transparent portion of the convex surface.

It will be appreciated that additional embodiments of methods may comprise any combination of the acts and features presented above and additional acts and features described below. Some acts and features presented above may be omitted in some embodiments, and some acts and features described below may be added in some embodiments.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

Various aspects, embodiments, and features of the present teachings can be more fully understood from the following description in conjunction with the accompanying drawings, in which.

DETAILED DESCRIPTION

I. Apparatus for Measuring Capillary Refill Time

The inventors have conceived of and developed improved apparatus and methods for measuring capillary refill time (CRT) of a patient or subject. The measurement may be carried out in an automated or semi-automated manner. The measurement results may be used by a physician to evaluate the extent or degree of an etiology related to generalized hypo-perfusion, e.g., dehydration, sepsis, heart disease, heart failure, or shock, and determine the need for medical intervention. The measurement results may also be used to quantitatively follow patients or subjects after intervention to assess the effectiveness of medical treatment. Of course, a physician or other care giver may use the results for other purposes, as the invention is not limited in this regard. The apparatus and methods provide reliable results regardless of skin pigmentation levels. In addition, the apparatus can be compact (e.g., a finger probe and associated controller).

In brief overview and according to one of the various embodiments, an apparatus for measuring capillary refill time comprises a measurement module containing at least two radiation sources and at least one detector configured to detect radiation from each source that interacts with and is received from a measurement region of a patient or subject. One radiation source may be characterized by a wavelength that is absorbed substantially equally by oxyhemoglobin and deoxyhemoglobin. The other radiation source may be used to provide a reference signal. For example, the detected signal from the first radiation source may be divided by, or into, the reference signal. The apparatus may further comprise controlling electronics (e.g., at least one processor to receive and process detected signals from the two radiation sources). The measurement module may be applied against a measurement region of a patient for a first time period, and then released from the measurement region for a second time period. Signals may be received and processed by the controller during each time period to determine a quantitative value for capillary refill time.

Figure 1:
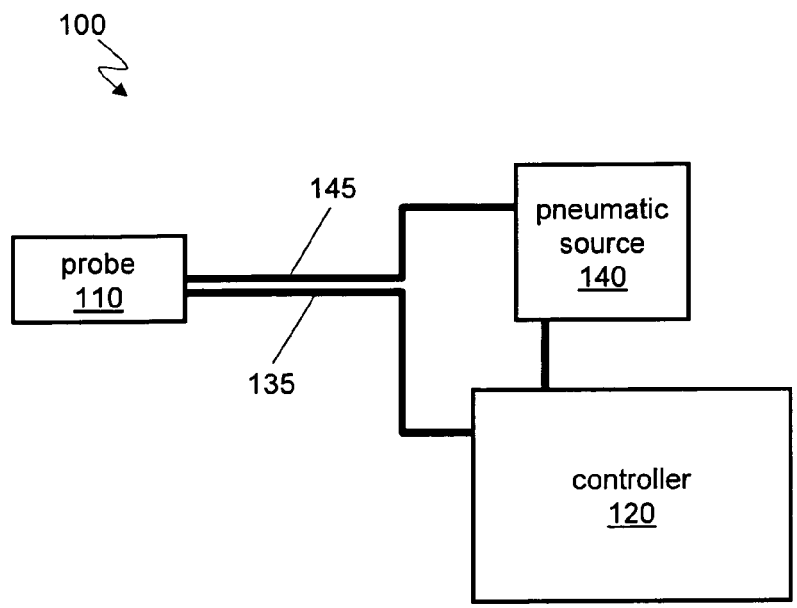
FIG. 1 illustrates, in block diagram form, an apparatus for measuring capillary refill time according to one embodiment.

In overview, FIG. 1 depicts, in block diagram, an embodiment of an apparatus 100 for measuring capillary refill time. The apparatus 100 comprises a probe 110 and a controller 120. The probe 110 may be placed in contact with a patient to sense at least one signal related to capillary filling. The controller 120 may be separate from the probe (as shown in FIG. 1) in some embodiments, or may be combined in one physical assembly with the probe in other embodiments (not shown). The controller 120 may include at least one processor and be configured to manage, at least in part, operation of the apparatus 100 and receive and process signals from the probe related to capillary refill time. The controller and probe may communicate through a communication link 135. The communication link 135 may comprise a wire, cable, fiber-optic link, or wireless link (e.g., RF, optical, ultrasonic link) suitable for carrying data signals and/or power. In some embodiments, the apparatus 100 may comprise a pneumatic source 140 for actuating components of the probe 110. The pneumatic source 140 may or may not be in communication with the controller, and may be configured to provide pressure and/or vacuum to the probe 110 through a pneumatic link 145. More specific details of each of the components will be described in more detail below.

In various embodiments, the probe 110 is adapted such that at least a portion of the probe may be placed in contact with a measurement region of a patient or subject to detect at least one signal related to capillary refill time. The measurement region may be any selected location on a patient or subject, and the probe 110 may be provided in any suitable shape for placing in contact with the measurement region. Some embodiments of probes and probe components are illustrated in FIGS. 2A-2F, although the invention should not be limited to only the structures depicted.

Figure 2A:
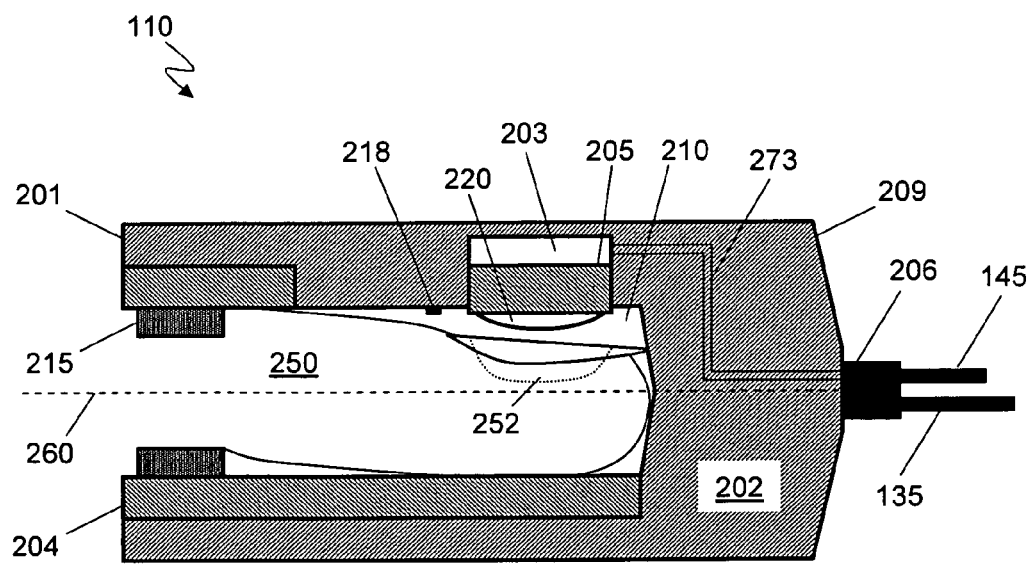
FIG. 2A depicts a probe for use in measuring capillary refill time.
Figure 2B:
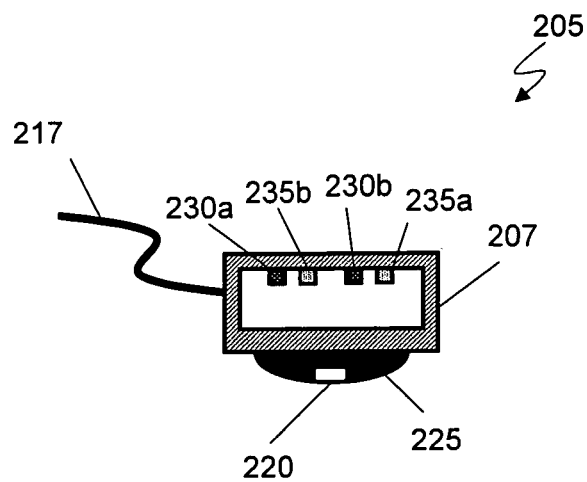
FIGS. 2B-2C depict various embodiments of components of a probe for use in measuring capillary refill time.
Figure 2C:
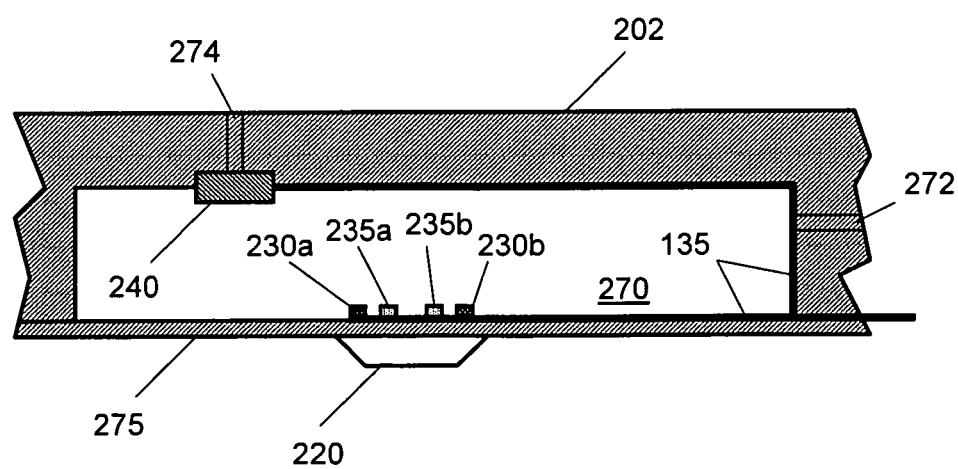
Figure 2D:
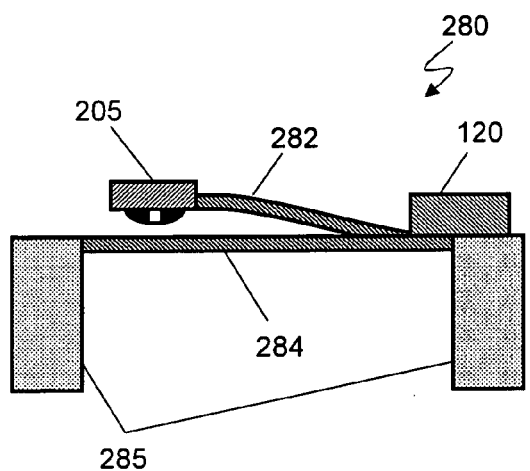
FIGS. 2D-2F depict an apparatus for measuring capillary refill time.
Figure 2E:
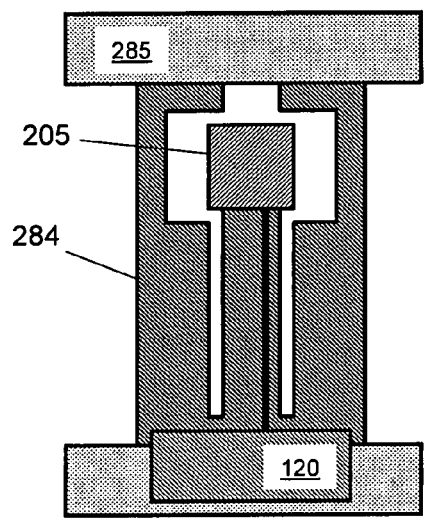
Figure 2F:
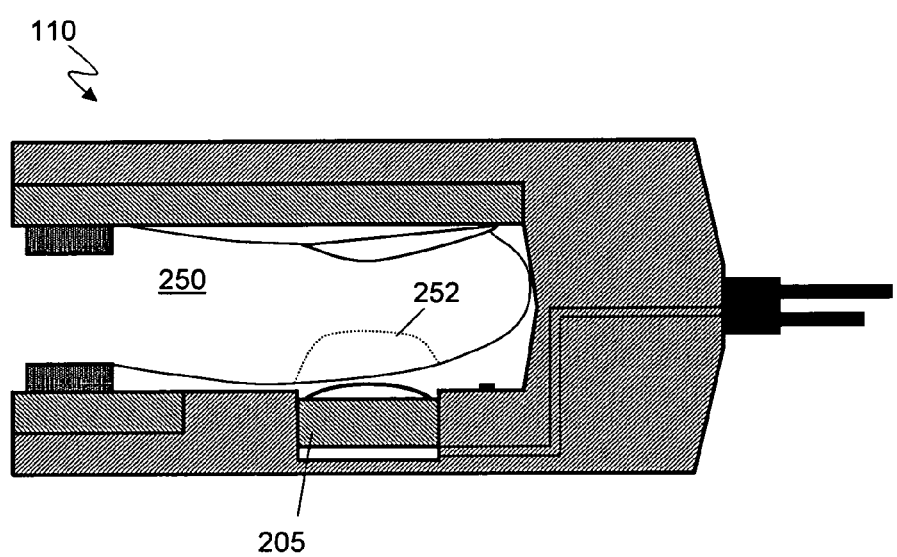

In some embodiments, the probe may be configured to fit over the patient's finger or toe as depicted in FIG. 2A or FIG. 2F, and include a probe housing 202 or structure to hold various measurement components 218, 205. In one embodiment, the probe includes a cylindrically-shaped probe housing 202 (although other shapes may be used, as the present invention is not limited in this regard) with a cavity 210 suitable to receive a measurement region 252 of a patient. The housing 202 may also include a separable insert 204 that adapts the housing to accommodate a wide variety of finger or toe sizes. In this regard, for adult or larger patients, a first insert may be used to provide a larger cavity 210, whereas for children or smaller patients, a second insert may provide a smaller cavity. The probe housing 202 may include a snap receptacle to lock the insert therewithin. In some implementations, the probe 110 may not include an insert 204, and may be provided in a wide variety of sizes.

The housing 202 may be close ended, such as depicted at end 209. This closed end can provide a stop for the positioning of a finger or toe in the probe 110 and thus aligning the measurement components over the desired measurement region. The length of the cavity 210 may be any value from about one-half inch to about three inches, depending upon the location of the capillary bed to be measured. In some cases, the cavity 210 may be as long as 5 inches, again depending upon the location of the desired measurement region. The cavity 210 may be circular or oval in cross section. In some embodiments, the cavity may extend all the way through the probe housing 202.

The housing 202 (and insert 204) may be formed of any suitable material, as the present invention is not limited in this regard. For example, the housing may be formed of materials that are easily manufactured, low cost and lightweight. In one embodiment, the housing and/or insert are formed of a plastic or polymeric material. Other suitable materials include composites, metals, ceramics, glass, or any combination thereof. In one embodiment, the housing is formed of a material having an opacity or other characteristic that substantially blocks undesirable light or radiation, e.g., light or radiation having a wavelength between about 300 nanometers (nm) and about 1500 nm.

The probe housing 202 and/or insert 204 may include a sealing member 215 to block unwanted radiation (e.g., ambient or background radiation). In one embodiment, the sealing member 215 conforms around a finger or toe to inhibit admission of light or radiation in a wavelength range between about 300 nm and about 1500 nm into the cavity 210. The sealing member may be formed of any suitable material, such as foam, fabric, a soft polymer, or combination thereof.

It may be desirable to use a plurality of different probes 110 with a single controller 120. In this regard, the housing 202 may be separable from the control electronics and pneumatics. In some implementations, one or more connectors 206 may be provided with the housing 202 for connecting or disconnecting the probe from the communication link 135 and/or the pneumatic link 145. In other implementations, the communication link 135 and/or the pneumatic link 145 may be permanently attached to the probe housing 202 and connectable and disconnectable at the controller 120.

According to one embodiment, the probe housing 202 may include pneumatic elements for actuating at least one measurement module 205. The measurement of capillary refill time may include moving the measurement module 205 into contact with a measurement region 252 of a patient or subject and releasing the measurement module from the measurement region. In this regard, pneumatic elements in the probe may include at least one pneumatic port 273 for conveying pressurize air or vacuum, and a pneumatic chamber 203. The application of pressure or vacuum to the pneumatic chamber 203 may move the measurement module 205 into contact with the measurement region 252, similar to piston action, or retract the measurement module from the measurement region. The module 205 may be retracted by applying vacuum to the recess 203. The pneumatic port 273 may connect to the pneumatic link 145.

Pressure and vacuum may be provided through pneumatic link 145 by a pneumatic source 140, in reference to FIG. 1. The pneumatic source may comprise a pump configured to provide pressure and/or vacuum. In some implementations, the pneumatic source may comprise electronically-controlled valves configured to control pressure and vacuum provided by an external source, e.g., a pressure and/or vacuum source at a facility. The pneumatic link 145 may comprise flexible tubing. In some implementations, the pneumatic link 145 may further include a wire, cable, fiber-optic link, or wireless link (e.g., RF, optical, ultrasonic link) suitable for carrying data signals and/or power. According to some embodiments, the pneumatic source 140 may be incorporated as part of the controller 120.

Although the application and retraction of the measurement module 205 may be obtained using pneumatic apparatus, other techniques and apparatus may be used to move the measurement module. For example, electromagnetic actuators (e.g., a solenoid) and apparatus may be used, manual operation by a physician or patient may be used, hydraulic actuators and apparatus may be used, electric motors and related drive components (e.g., a screw turned by the motor), electric motor driven actuators, piezoelectric actuators, etc.

The probe 110 may include a temperature sensor 218 for sensing a temperature near the measurement region 252. The skin temperature of the measurement region may affect the capillary refill time. For example, a lower skin temperature generally impedes perfusion and can cause a lengthening of capillary refill time. A value of temperature measured in the vicinity of the measurement region 252 may be used by the controller 120 to correct a measured value of capillary refill time. The temperature sensor 218 may comprise a thermistor, an infrared sensor, or any other suitable thermal sensing arrangement. A signal from the temperature sensor 218 may be provided to the controller 120 (e.g., through communication link 135) for processing to determine a temperature in the vicinity of the measurement region 252.

According to one embodiment, the temperature sensor 218 may be mounted on an internal surface of the probe proximal to the measurement region 252 so as to measure a temperature representative of the temperature of the measurement region. In such an embodiment, a probe made of low density material, insulating material, or a material having low heat capacity, may improve the accuracy of temperature sensed by the sensor 218, e.g., the sensed temperature may be mainly influenced by the temperature of the finger, toe, or measurement region, rather than the probe.

In some implementations, the temperature sensor 218 may be separately attachable to a measurement region 252 or location on a patient or subject in the vicinity of the measurement region. In some cases, the temperature sensor 218 may be disposed on a flexible member that contacts the patient (e.g., a flexible arm that brings the sensor into contact with the patient's finger or toe when inserted into the probe 110). In some embodiments, the temperature sensor may be disposed on the measurement module 205 such that it contacts the measurement region 252 when the measurement module is moved into contact with the measurement region.

In some embodiments, the controller 120 may be adapted to receive addition patient diagnostic input that may affect capillary refill time. Additional input may include patient blood pressure. Additional patient diagnostic input may be used by the controller 120 to correct measured capillary refill time. Additional patient diagnostic input may be sensed, in some cases, at the probe (e.g., heart rate, blood oxygen level), or may be input by a user at the controller.

In various embodiments, the probe 110 includes a measurement module 205 having a contact member 220 that may be moved into contact with a measurement region 252 of the patient and retracted from the measurement region. The measurement module 205 may include at least a portion of the electronics and optical devices that are used to sense capillary refill time. The measurement module 205 may be in communication with the controller 120 (e.g., through communication link 135) to receive power and/or signals for controlling the electronics and optical devices associated with the module 205 and to provide sensed signals and/or data relating to capillary refill time.

FIG. 2B illustrates one embodiment of a measurement module 205 that may be used in sensing capillary refill time. The measurement module may comprise a module housing 207 to which the contact member 220 may be affixed. Mounted inside the module housing 207 may be at least one radiation source 230a, 230b and at least one detector 235a, 235b that are employed in measurements of capillary refill time. In this regard, the at least one radiation source 230a, 230b and at least one detector 235a, 235b may be in communication with the controller 120 through a communication link 217. The communication link 217 may be a flexible wire, cable, fiber-optic link, or wireless link, and be connected to, or part of, communication link 135 to the controller 120. The measurement module may be disposed in a probe 110, or in some cases used manually, e.g., used without a probe housing 202 and related structure.

When included with a probe 110 as depicted in FIG. 2A, the measurement module 205 may be disposed at any location within the cavity 210 of the probe. Although shown near a nail of a finger in the drawing, the measurement module may be located elsewhere, e.g., beyond the nail towards the first joint, near a joint, near a knuckle, on a side of the finger, near the pad of the finger.

The module housing 207 may be provided in any shape, e.g., square, rectangular, polygonal, circular, oval, and formed from any suitable material or composite, e.g., a polymer, metal, ceramic, glass, or any combination thereof. For the embodiment shown in FIG. 2A, the module housing may fit into a recess 203 of the probe housing 202 with close tolerance so as to form a substantially air-tight seal. In this arrangement, the measurement module 205 may be moved into contact with a measurement region 252 and retracted from the measurement region, as described above.

In preferred embodiments, a first radiation source 230a and a second radiation source 230b are included with the measurement module 205 and configured to provide radiation to illuminate and interact with the measurement region 252. Radiation received from the measurement region may be detected and signals processed to yield a measurement of capillary refill time. Either radiation source may be a semiconductor or organic light-emitting device, e.g., a light-emitting diode (LED), an organic light-emitting diode (OLED), a phosphorescent organic light-emitting diode (PHOLED), or a semiconductor or organic laser diode. Each radiation source may be controlled by at least one processor in the controller 120. The radiation sources 230a, 230b may be provided in an integrated package or as separate components, and may be mounted in, on, or in close proximity to the measurement module 205. There may be provided at least one diffusing optic (e.g., a diffuser mounted with each radiation source or incorporated with the contact member 220) for homogenizing the intensity of radiation emitted from the measurement module.

Figure 3A:
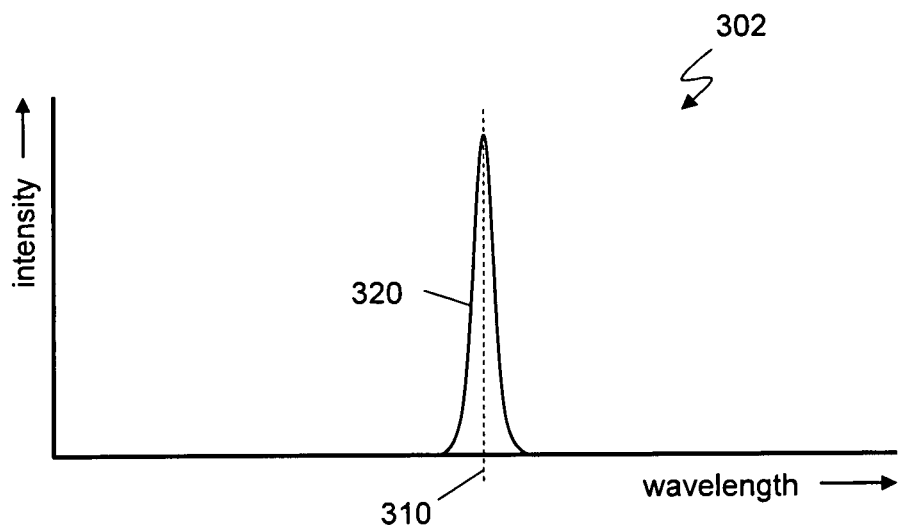
FIG. 3A depicts an emission spectrum of a radiation source.

The first radiation source 230a may be characterized by a first wavelength $\lambda_1$, and selected to preferentially interact with blood contained within the tissue, e.g., blood within capillary beds. The term "characterized by a wavelength" is used herein to refer to a central or characteristic wavelength emitted from a radiation source. A radiation source may emit a distribution of wavelengths within a narrow band 320, as depicted in FIG. 3A. The source may be characterized by a dominant wavelength or central wavelength 310. In some embodiments, the first source is characterized by a first wavelength $\lambda_1$ in a range between about 490 nm and about 560 nm, or between about 500 nm and about 550 nm, or between about 500 nm and about 530 nm. In some implementations, the first source is characterized by a first wavelength $\lambda_1$ in a range between about 513 nm and about 523 nm. In some embodiments, the first source is characterized by a first wavelength $\lambda_1$ of approximately 518 nm.

Figure 3B:
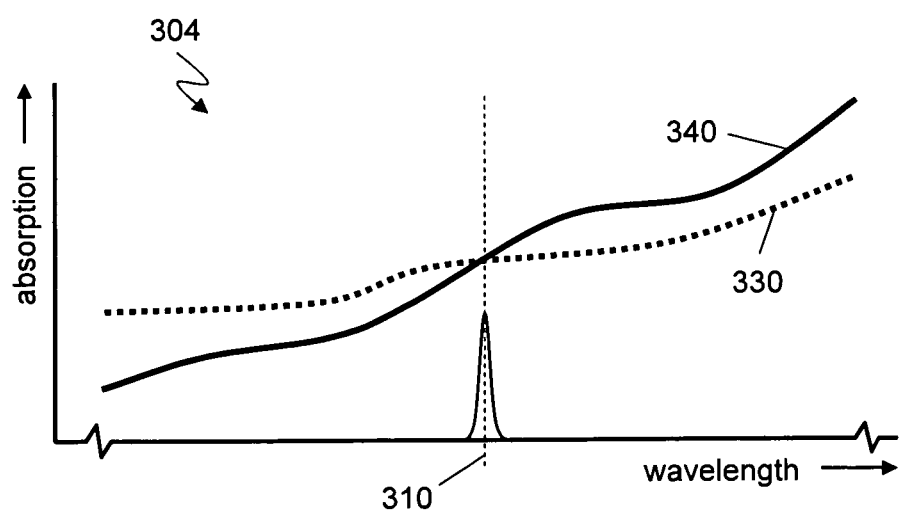
FIG. 3B depicts absorption characteristics of oxyhemoglobin and deoxyhemoglobin.

The inventors have discovered that employing a first radiation source based on absorption characteristics of oxyhemoglobin and deoxyhemoglobin allows a measurement of blood in a capillary bed that will not preferentially sense pre-capillary aertioles or post-capillary venules. A graph 304 of absorption characteristics of oxyhemoglobin and deoxyhemoglobin is depicted in FIG. 3B for a limited range of wavelengths. In this range, the absorption curve 330 for oxyhemoglobin crosses the absorption curve 340 for deoxyhemoglobin. The first radiation source (superimposed on the graph 304) is selected so that its characteristic wavelength 310 is located at approximately the crossing point of the absorption curves. As such, the absorption of the first radiation is approximately equal for equal amounts of oxyhemoglobin and deoxyhemoglobin. The absorption of the first radiation may be equal to within about 20%, within about 10%, within about 5%, and yet within about 2% in some implementations for equal amounts of oxyhemoglobin and deoxyhemoglobin.

The penetration depth of the first radiation and/or the second radiation in tissue may be in a range between about 50 microns and about 5 millimeters. In some embodiments, the first radiation source and/or second radiation source may be selected based, at least in part, upon the penetration depth of the first radiation and/or second radiation in tissue.

In some implementations, an amount of the first radiation absorbed in a measurement region is proportional to an amount of blood within the measurement region. In this regard, an amount of the first radiation transmitted through a measurement region may be inversely proportional to an amount of blood within the measurement region. In some cases, an amount of the first radiation returned or reflected from a measurement region is inversely proportional to an amount of blood within the measurement region.

The use of a second radiation source to provide a reference signal can improve measurement consistency and reliability. A signal ratio of the first radiation source and second radiation source may compare received first radiation that primarily interacts with blood within the measurement region to received second radiation that primarily interacts with tissue and/or a tissue surface in the measurement region. Since the tissue and/or tissue surface may affect the received first radiation, the ratio or comparison can be used to substantially cancel tissue and/or tissue surface artifacts from a measurement of capillary refill time. Additionally, artifacts in measurements that could arise from different measurement regions (e.g., different patients, different skin texture, different skin color, different skin surface configuration, different skin-to-measurement module configurations) can be substantially canceled using a second radiation source.

The second radiation source 230b may be characterized by a second wavelength $\lambda_2$, and selected such that its characteristic wavelength is substantially unaffected by the presence or absence of blood in the measurement region. A second radiation source may be chosen such that its characteristic wavelength preferentially interacts with tissue and/or the tissue surface region in a measurement region 252 rather than blood within the measurement region. The second radiation may be absorbed, scattered, re-emitted, or reflected near the surface of a measurement region, e.g., above a capillary bed. The second source may be characterized by a second wavelength $\lambda_2$ in a range between about 610 nm and about 710 nm, or about 600 nm and about 750 nm. In some implementations, the second source is characterized by a second wavelength $\lambda_2$ in a range between about 640 nm and about 680 nm. In some embodiments, the second source is characterized by a second wavelength $\lambda_2$ of approximately 660 nm.

In some implementations, the second radiation source may be characterized by a wavelength that is shorter than the first radiation source, e.g., between about 300 nm and about 500 nm. The second radiation source may be selected such that its characteristic wavelength has an absorption depth in tissue on the order of a distance $d_c$ from the skin surface to a region of the tissue having a dense concentration of capillaries. For example, the second radiation source may be selected such that its characteristic wavelength has an absorption depth between about $1 \times d_c$ and about $2 \times d_c$, between about $2 \times d_c$ and about $3 \times d_c$, or between about $3 \times d_c$ and about $4 \times d_c$. A shorter wavelength may be more sensitive to surface effects of the measurement region and, when used as a reference signal, may improve cancellation of measurement artifacts related to surface effects.

In some implementations, there may be three radiation sources. The first radiation source may be characterized by a wavelength between about 500 nm and about 540 nm. The second radiation source may be characterized by a wavelength between about 300 nm and about 500 nm. The third radiation source may be characterized by a wavelength between about 550 nm and about 1500 nm. Detected signals representative of the second and third radiations received from the measurement region may be combined (e.g., averaged in some manner) and divided into, or divided by, a detected signal representative of the first radiation received from the measurement region in some embodiments. Alternatively, detected signals representative of the second and third radiations may be processed separately (e.g., the radiation source may be characterized by a wavelength between about 400 nm and about 500 nm) and may be used to determine the melanin content of the measurement region.

The measurement module 205 may further include, in some embodiments, a radiation source suitable for pulse oximetry. The radiation source may be characterized by a wavelength in a range between about 915 nm and about 965 nm, or about 900 nm and about 950 nm. This radiation source may be used in combination with at least one of the radiation sources selected for measuring CRT to carry out pulse oximetry measurements. A detector may be included in the measurement module 205 to detect radiation from the source suitable for pulse oximetry returned from the measurement region 252 or the detector may be mounted separately from the measurement module to detect the radiation transmitted through or scattered from the measurement region.

Although the radiation sources 230a, 230b are shown as separate sources, the radiation sources may be provided as a single multi-color source, e.g., a white-light source that emits a broad range of wavelengths spanning the characteristic wavelengths of the first radiation and second radiation, and third radiation as described above (e.g., a broad band including wavelengths in the vicinity of 518 nm and 660 nm, and 950 nm) or a bi- or tri-color source that emits discrete bands of wavelengths in the vicinity of the characteristic wavelengths of the first radiation and second radiation, and third radiation (e.g., including a narrow band of emission around 518 nm and a narrow band of emission around 660 nm. When provided as a single multi-color source, wavelength filtering at the detectors may be used to detect signals received from the measurement region 252 corresponding to each desired wavelength, e.g., a first signal corresponding to 518 nm and a second signal corresponding to 660 nm, as described below.

Radiation from the at least one radiation source may be detected by at least one detector 235a, 235b for providing at least one signal to the controller 120. The at least one detector may be contained within the measurement module 205 and/or mounted at another location within the probe 110 (e.g., a detector mounted to receive radiation transmitted through the measurement region). The at least one detector may be configured to detect first radiation received from the measurement region 252 or second radiation received from the measurement region. In some implementations, the at least one detector may be configured to detect first and second radiation received from the measurement region. The term "radiation received from the measurement region" is used to refer to any manner in which radiation originating from a radiation source 230a, 230b may be received from a measurement region 252 (e.g., reflected, transmitted, scattered, re-emitted).

In some embodiments, the measurement module may include at least one first detector 235a sensitive to the first radiation source 230a and at least one second detector 235b sensitive to the second radiation source 230b, so that the first and second radiation sources may be activated simultaneously. For example, the at least one first detector 235a may be provided with a narrow band filter that transmits substantially only wavelengths in a first narrow band corresponding to the first radiation source, and the at least one second detector 235b may be provided with a second narrow band filter that transmits substantially only wavelengths in a narrow band corresponding to the second radiation source. In such embodiments, the first radiation source and second radiation source may be activated during at least one common time interval, and radiations received from the measurement region may be detected in at least one common time interval.

In some implementations, one detector is provided with the measurement module 205. For example, the detector 235a may be mounted to detect first or second radiation returned from the measurement region. The term "returned from the measurement region" is used to refer to receiving radiation back from a measurement region, generally in a direction opposite the illuminating radiation, and may refer to reflected, scattered, or re-emitted radiation. When one detector is used, the first and second radiation sources may be activated at separate time intervals in a time-division multiplexing manner. For example, the first radiation source 230a may be turned on for a first interval and a first signal detected with the one detector 235a. The first source 230a may then be turned off and the second source 230b turned on for a second time interval and a second signal detected with the one detector 235b. The first and second signals may be recorded by the controller 120 for subsequent processing.

Any suitable type of detector may be used. Each detector may comprise a semiconductor photodiode with or without amplification circuitry. Each detector 235a, 235b may comprise an avalanche photodiode and related circuitry. In some embodiments, a small photomultiplier may be used for each detector. A detector may be provided with an optical filter selected to pass radiation in a selected narrow band, e.g., a band approximately centered at a characteristic wavelength of one of the radiation sources 230a, 230b. A detector may also be provided in the measurement module 205 with electrical amplification and signal filtering.

Amplifying circuitry (not shown) may be included with the detectors to amplify any detected signal prior to transmitting the signal to the controller 120. The amplifying circuitry may be incorporated in the measurement module 205 or in the probe 110.

Any one of, or all of, the radiation sources may be configured to be modulated on and off at a rapid rate during a measurement of capillary refill time to improve signal quality and confidence in a measurement. Additionally, a signal from the at least one detector 235a, 235b may be sampled at a rapid rate. The sampling of a detected signal may be carried out by the controller 120. The sampling of a detected signal may be synchronized with modulation of a radiation source, and the sampling results averaged to reduce a noise level of the detected signal (e.g., utilize a lock-in detection technique). Any of the detected signals may be averaged over a selected time interval to reduce noise. The modulation, sampling, and averaging may be selected to improve the quality and accuracy of detected signals. Modulation of a radiation source may be controlled by the controller 120. The averaging and signal processing may be carried out by the controller. In some implementations, any one of, or all of, the radiation sources may be controlled to emit a substantially constant amount of radiation during a measurement.

In some implementation, the contact member 220 of the measurement module 205 includes a convex surface, as depicted in FIGS. 2A-2B. Employing a convex surface for the contact member 220 more readily excludes blood from a capillary bed when brought into contact with a measurement region. In this regard, a central, smaller area first contacts the measurement region 252, and, as more of the surface comes into contact with the measurement region upon application of increased pressure on the contact member 220, blood in the measurement region is pushed out of the region. The convex surface may be rounded, e.g., cylindrically convex, spherically convex, or parabolically convex. The contact member 220 may comprise a spherical or cylindrical lens. The curvature of the convex surface may be sharp or gradual. In some embodiments, the curvature may be stepwise, e.g., shaped like a multi-faced polygon, as depicted in FIG. 2C.

In various implementations, at least a portion of the contact member 220 transmits light or radiation in a wavelength range between about 300 nm and about 1500 nm. The contact member 220 may be fabricated from a transparent polymer or glass. In this regard, radiation from the at least one radiation source 230a, 230b may pass through the contact member 220, interact with the measurement region 252, and be transmitted through the measurement region or returned from the measurement region for detection. For the embodiment shown in FIG. 2A, radiation returned from the measurement region 252 may pass back through the contact member and be detected by the at least one detectors 235a, 235b of the measurement module.

The contact member 220 may or may not be partially covered with a material or film 225 for blocking or substantially reducing background radiation that may adversely affect a measurement of capillary refill time. In some embodiments, the film 225 may comprise a multilayer optical film that transmits at least one narrow band of radiation and blocks or substantially blocks radiation outside the narrow band. In some implementations, the film 225 may comprise a multilayer optical film that transmits a first narrow band of radiation corresponding to a first radiation source 235a and also transmits a second narrow band of radiation corresponding to a second radiation source 235b. For the embodiment shown in FIG. 2A, it may not be necessary to include a light-blocking film 225 on the contact member 220, since the probe housing 202 and sealing element 215 may substantially block background light or radiation. In some embodiments, the film 225 may comprise piezoelectric film that can block background light or radiation and sense a contact pressure between the contact member 220 and the measurement region 252.

In alternative embodiments, the contact member may comprise a concave shape, e.g., having an inward-deflected surface, and include a pneumatic port for applying vacuum at the location of the concave surface. When brought into contact with a measurement region, vacuum may be applied to "suck up" or draw the measurement region into the concave region of the contact member, so as to momentarily exclude at least a portion of blood from the measurement region. In some implementations, the contact member may further include mechanical apparatus to affect squeezing of tissue drawn into the concave shape so as to exclude at least a portion of blood from the measurement region. For example, a concave portion of the contact member may comprise a flexible suction member for drawing in a measurement region and electromechanical and/or pneumatic apparatus for pinching or squeezing the suction member and skin. Such a suction device may be used on portions of a body (e.g., chest, forehead, stomach) that may not accommodate apparatus as depicted in FIG. 2A.

Figure 3C:
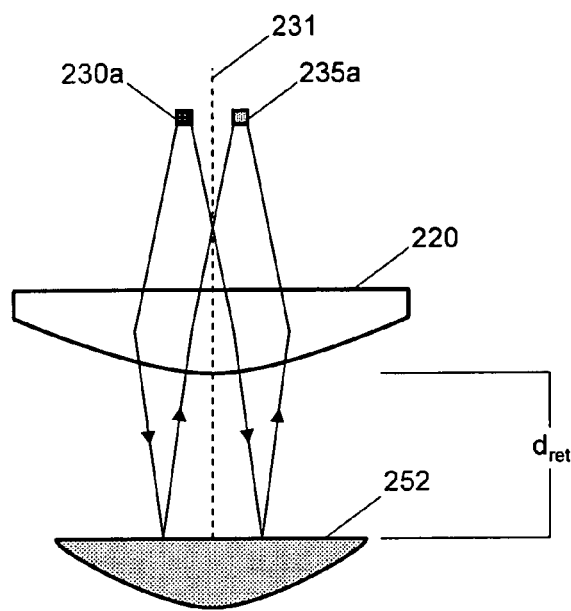
FIG. 3C depicts an optical arrangement of a radiation source, a detector for detecting the radiation source, and a contact member 220 that exhibits lensing action according to one embodiment.

The radiation sources 230a, 230b and detectors 235a, 235b may be configured in the measurement module 205 in conjunction with the contact member 220 to increase optical signal collection efficiency. The inventors have recognized that a contact member 220 having a convex surface can be utilized to collimate, partially collimate, focus, or partially focus radiation emitted from the radiation sources. For example, the contact member 220 may be a lens or exhibit lens-like action on incident radiation. A radiation source may be mounted near or at a focal surface of the contact member, so that radiation divergent from the source is substantially collimated after passing through the contact member. Additionally, radiation received from the measurement region may be focused or partially focused by the contact member 220, and a detector for the radiation source may be located near or at a focal region for the received radiation. In this regard, one embodiment of a mounting configuration for a radiation source 230a, corresponding detector 235a, and contact member that utilizes of a lensing effect of the contact member is depicted in FIG. 3C. In some implementations, a radiation source and the surface of the measurement region may be located at conjugate points of a lens (not shown, that may be separate from the contact member) provided with the measurement module.

According to one embodiment and in reference to FIG. 3C, the radiation sources and/or corresponding detectors may be located symmetrically about a central axis 231 of the measurement module to further improve signal quality. When the contact member 220 presses against the measurement region 252, it can leave a temporary divot in the measurement region. This temporary divot can affect the reflection, scattering, or transmission of radiation received from the measurement region. By symmetrically distributing the radiation sources and/or corresponding detectors, optical effects of the temporary divot can be substantially equal for detection of each source of radiation and may be canceled by taking a ratio of signals obtained from at least two sources of radiation received from the measurement region.

To symmetrically mount radiation sources, the distances from the central axis 231 may be the same for each radiation source. Similarly, detectors can be symmetrically mounted about a central or optical axis. In some implementations, each source and/or its corresponding detector may be mounted on opposite sides of at least one circle centered on the central axis 231. Further, the at least one circle may lie in a focal surface of the contact member. In some cases, there may be a plurality of radiation sources and corresponding detectors disposed in at least one ring around the central axis. If a single multi-color source is used, it may be mounted on the central or optical axis 231 and a plurality of detectors may be disposed in a ring around the central axis.

To further improve signal consistency and reliability, the measurement module may be configured within the probe 110 to be retracted so that the contact member 220 retreats a selected distance $d_{ret}$ from the surface of the measurement region 252 as shown in FIG. 3C. In some implementations, the distance $d_{ret}$ is substantially constant from patient to patient. A constant distance can improve signal reliability. The distance $d_{ret}$ may be in a range between about 1 mm and about 10 mm.

The measurement region 252 may comprise a region of the patient in the vicinity of the area that comes into contact with the contact member 220. Accordingly, the location of the contact member identifies the location of the measurement region 252 on a patient, or the choice of measurement region identifies where the contact member will be located. In various embodiments, the measurement region includes a capillary bed.

Figure 5A:
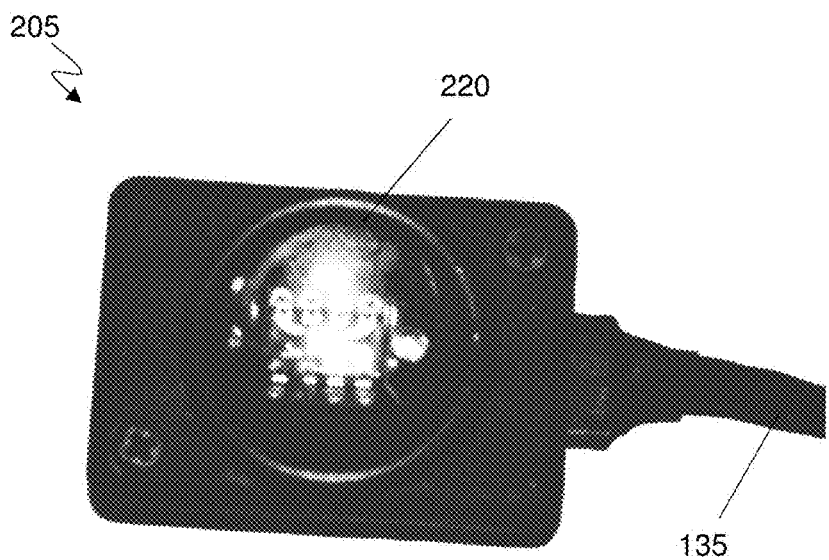
FIG. 5A shows an embodiment of a prototype probe.

Although the probe 110 is shown in FIG. 2A in a cylindrical form that can receive at least a portion of a finger or toe, the probe may take any of a variety of alternative shapes and forms. For example the probe 110 may be in the form of a clip-on device, e.g., formed like a clothespin, that clips onto a finger or toe. Alternatively, the probe 110 may be in the form of a band that may be placed around or wrapped around a finger, toe, wrist, ankle, arm portion, or leg portion. In some embodiments, the probe 110 may be a simple device as shown in FIG. 5A that is manually pressed against a measurement region 252 of a patient and released from the measurement region. Additionally, components within the probe and/or measurement module may be arranged in any suitable manner for measuring capillary refill time.

FIG. 2C depicts a cross-sectional and elevation view of an alternative embodiment of measurement module components incorporated in a probe (e.g., into the probe housing 202 of FIG. 2A). In this embodiment, the contact member 220, radiation sources 230a, 230b, and detectors 235a, 235b are disposed on a flexural member 275 that is sealed against a pneumatic chamber 270. In operation, pressurization of the chamber 270 may force the flexural member 275 outwards and into contact with a measurement region of a patient. Release of pressure from the chamber 270, and/or the application of vacuum to the chamber, may withdraw the contact member from the measurement region. Pressure and vacuum may be applied to the chamber 270 through a pneumatic port 272. Pressure may be released quickly from the chamber through a valve 240 and exhaust port 274. The valve may be electronically controlled by the controller 120 via link 135. If vacuum is used to withdraw the contact member 220, the valve and exhaust port may not be included.

Measurement consistency may be improved by including pressure and/or vacuum (e.g., piezoelectric sensor, pressure activated switch) with the apparatus of FIG. 2C and FIG. 2A. The pressure and/or vacuum sensors may be used to sense pressure and/or vacuum at the chamber 270, 203 or along a pneumatic line connected to the chamber, so that contact pressure can be made substantially constant from patient to patient. Additionally, a retracted distance may be made substantially constant by monitoring vacuum pressure.

An additional embodiment of an apparatus 280 for measuring capillary refill time is depicted in FIGS. 2D-2E. FIG. 2D portrays an elevation view, and FIG. 2E depicts a plan view of the apparatus that may be used as a stand alone device. The apparatus 280 may be powered by an on-board battery, and operated semi-automatically. The apparatus 280 may be used in a clinical setting, or outside a clinical setting, e.g., by a parent in a household setting.

The apparatus 280 of FIGS. 2D-2E or the measurement module 205 may be used to measure capillary refill time at measurement regions other than those located at an extremity of a patient. For example, the apparatus 280, or module 205 used manually, may be used to measure capillary refill time at a measurement region on the torso of a patient. This can be useful for obtaining a comparison of capillary refill times measured at an extremity (e.g., finger or toe), mid appendage (e.g., mid arm or mid leg), and core or torso.

Referring again to FIGS. 2D-2E, the apparatus 280 may include both a measurement module 205 and controller 120 attached to a flexible structure. The flexible structure may include a base portion 284 and a flexible arm 282. The measurement module 205 may be disposed on the flexible arm 282 such that it may be pressed manually against a measurement region 252 of a patient. The module may be pressed by a physician or a patient. When released, the flexible arm may retract the measurement module from the measurement region. The apparatus may include at least one elastic band or Velcro strap 285 for securing the apparatus to a patient. The apparatus 280 may be secured to a finger, toe, foot, hand, lower leg, forearm, or other suitable area of a patient. In some embodiments, the apparatus may include light-blocking fabric covering most or all of the apparatus.

For the apparatus 280 of FIGS. 2D-2E, the controller may include a simple display, e.g., an LCD three- or four-digit display, and an on-off button. The controller may be configured to display "PRES" when ready to begin a measurement. This may instruct a physician or patient to press the measurement module against a measurement region. The controller may be configured to display "REL" to instruct the physician or patient to release the measurement module. The controller may then process received signals, calculate a value of CRT, and then display the calculated value in seconds (e.g., "1.52" or "1.5 S", "3.66" or "3.7 S") The display may present a blinking or constant cursor when obtaining data, and a same or different cursor when calculating results. The apparatus may alternatively or additionally include audio and/or tactile signals to instruct a user in device operation.

Figure 4:
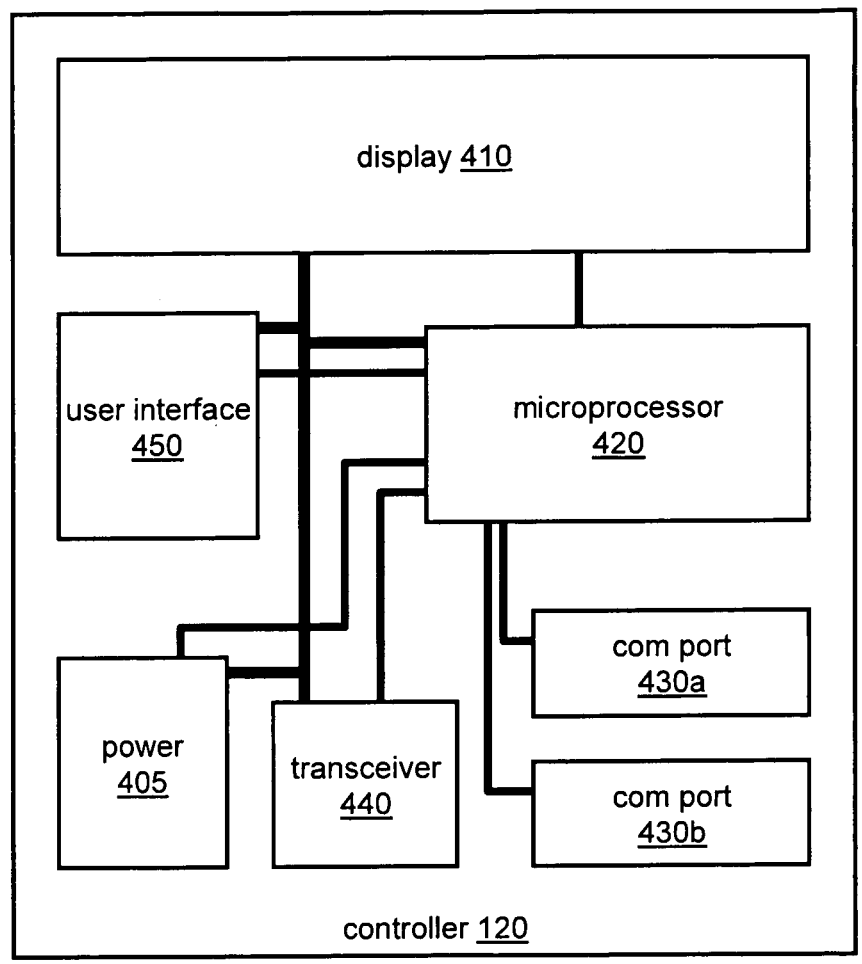
FIG. 4 depicts a controller that may interface with the probe 110, according to one embodiment.

FIG. 4 depicts, in block diagram, an embodiment of a controller 120 that may be used in conjunction with the probe 110 for measuring capillary refill time. The controller may manage operation of the probe and/or pneumatic system 140. Further, the controller may store and/or process data received from the probe to determine capillary refill time. Additionally, the controller may store computed capillary refill time. In overview and according to one embodiment, the controller 120 may include a display 410, a user interface 450, a microprocessor 420, and a power source or power jack 405. The controller may further include at least one communication port 430a and/or a transceiver. The controller may further include memory (not shown) for storing data for subsequent retrieval.

The display 410 of the controller may comprise any type and form of visual and/or audio display for displaying or providing instructions to a user. The display may also be used to display or provide data to a user during operation of the measurement apparatus 100. The display may comprise a multi-digit display (e.g., an LCD single-color digital display) or may comprise a small display for displaying video data. An example of a single-color display may be part number LCD-S401C39TR available from Lumex Opto/Components Inc. of Palatine, Ill. An example of a small video display may be part number LQ030B7DD01 available from Sharp Microelectronics at Camas, Wash. The display 410 may be in communication with the microprocessor 420 and receive power from the power source 405.

The user interface 450 may be any type and form of user interface by which a user may enter data or execute actions to operate the controller 120. The user interface may comprise at least one on/off switch. The user interface may include any one of or a combination of a key pad, a touchpad, a trackball, and a touch screen. The user interface may include a microphone, and the controller may be equipped with voice recognition capability. The user interface 450 may be in communication with the microprocessor 420, and may or may not receive power from the power source 405.

Figure 7:
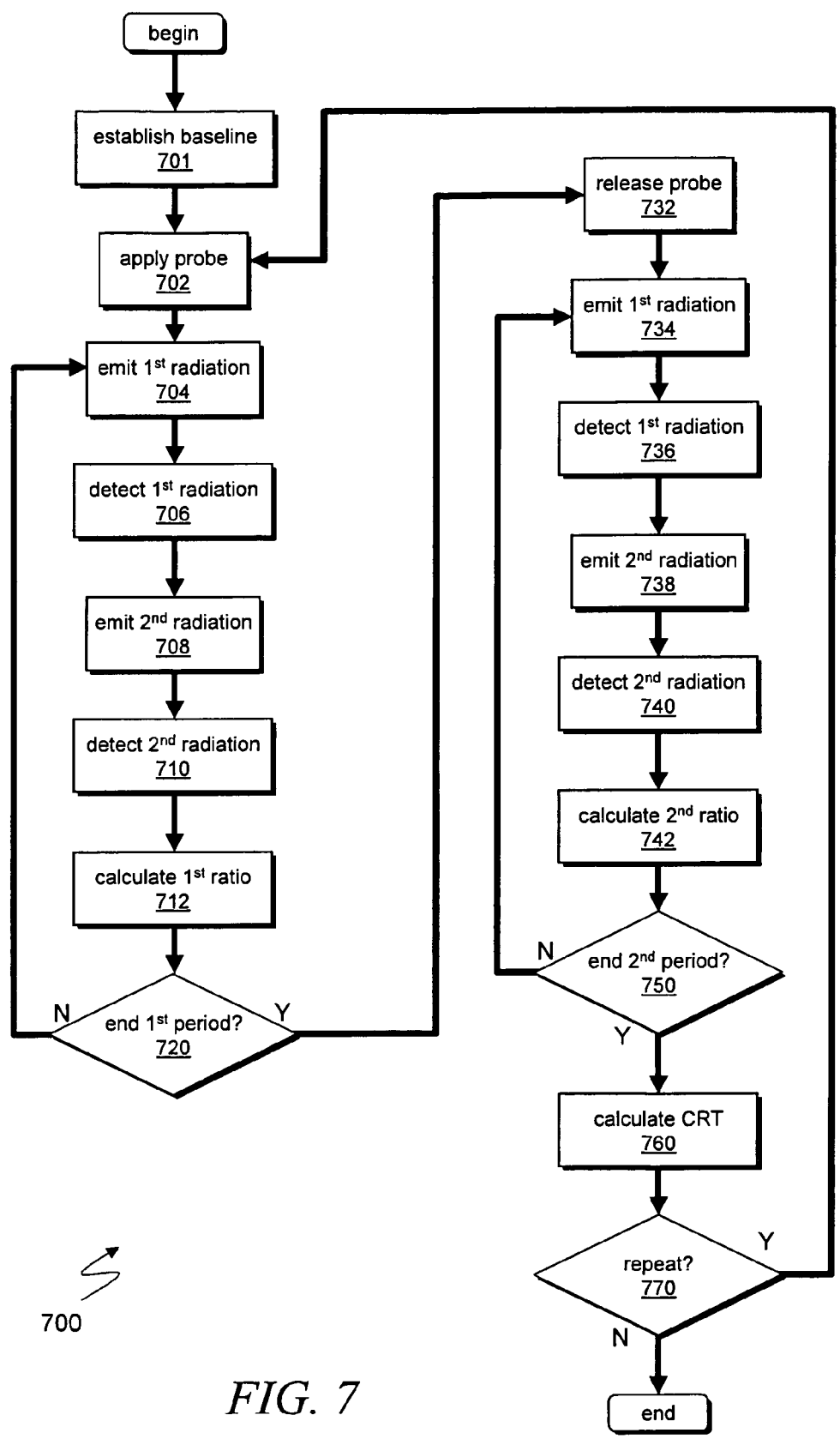
FIG. 7 is a flow diagram of a method for measuring capillary refill time, according to one embodiment.

The microprocessor 420 may comprise at least one processor that can receive machine-readable instructions and execute acts for controlling and operating various aspects of the measurement apparatus 100 responsive to the instructions. The microprocessor may comprise a microcontroller module, e.g., part number BS2E-IC available from Parallax, Inc. of Rocklin, Calif. The microprocessor 420 may be in communication with a plurality of components of the controller 120, as shown in FIG. 4, and may receive power from the power source 405. The microprocessor 420 may be programmable and configured to receive machine-readable instructions, e.g., via transceiver 440 or a communication port 430a, 430b. Machine-readable instructions for the microprocessor 420 may comprise any one of, or any combination of, instructions representative of the acts described below in connection with FIG. 7 as well as other acts described herein relating to measurement and calculation of capillary refill time.

The controller 120 may further include at least one of, or a combination of, a communication port 430a and a transceiver 440 for exchanging data with an external device and/or the probe 110. For example, the communication port and/or transceiver may be used to control the probe and receive signals from the probe. The communication port and/or transceiver may be used to communicate with another processor, e.g., for obtaining data from the controller 120 and/or for programming the microprocessor 420. The communication ports may comprise USB ports or any suitable multi-pin ports. Connection hardware may also be provided with the controller for attaching a cable, e.g. attaching a USB cable or multi-wire cable to the controller to connect to a communication port. The at least one communication port and/or transceiver may be connected to the microprocessor 420.

Results of CRT measurements may be stored on the controller for subsequent processing or comparison. For example, CRT results may be analyzed for trends, averages, or other statistical factors. CRT results may also be compared with population norms.

Figure 5B:
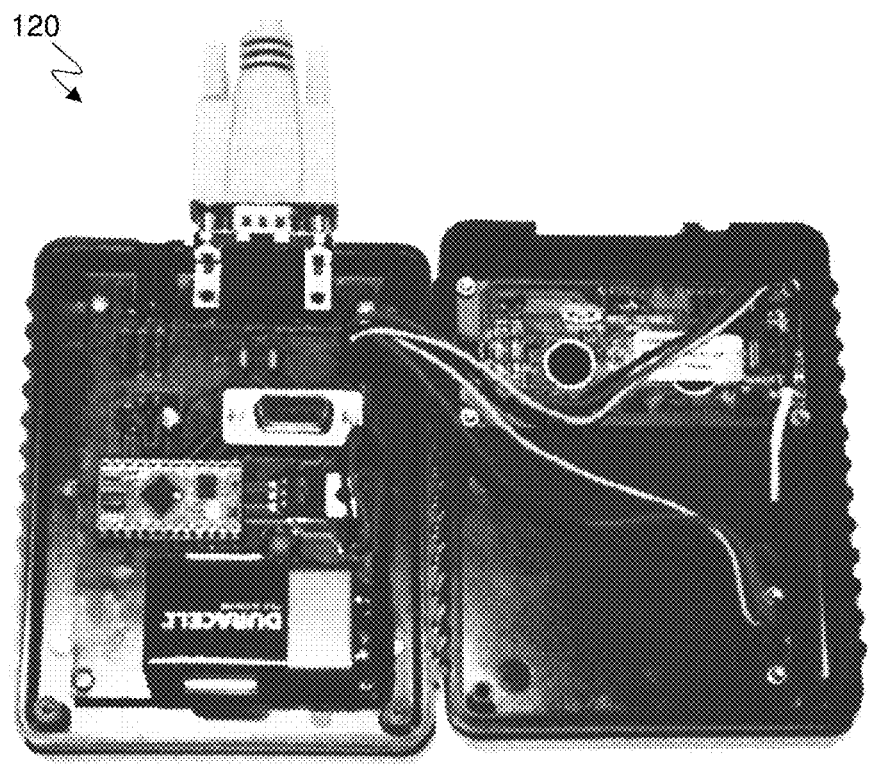
FIG. 5B shows an embodiment of a prototype controller for measuring capillary refill time.

The inventors developed a prototype probe and controller for measuring capillary refill time, and photoimages of the device are shown in FIGS. 5A-5B. The prototype is a hand-held device, wherein the probe 110 is manually applied to a measurement region of a patient. The probe is enlarged in FIG. 5A, and the actual device measures about 30 mm on its short side. The probe 110 comprises a measurement module and includes a spherically shaped and transparent contact member 220. Radiation sources and detectors are mounted in the module behind the contact member. The module is connectable to the controller with a multi-wire cable 135 and associated connectors at each end of the cable.

The prototype controller 120 is shown in FIG. 5B. The controller includes an on-board 9V battery, which is visible in the photoimage and provides a size reference for the controller. The controller also includes a digital display, an on/off switch, two communication ports, and a microcontroller module.

In some implementations, the controller 120 may be a stand-alone or hand-held device. In alternative embodiments, the controller may comprise a computer with at least one processor adapted to execute the functionality of the controller 120 as described above. In some embodiments, the controller may be incorporated in or added to, as hardware, software, or a combination thereof, existing medical electronic equipment (e.g., bedside monitoring instruments, blood-pressure monitoring apparatus, heart-rate monitoring apparatus, pulse oximetry apparatus, operating room equipment, etc.)

III. Operation

An overview of operation of apparatus 100 for measuring capillary refill time will now be described in reference to FIG. 6, which depicts ideal measurement signals for a measurement of capillary refill time. To facilitate understanding, radiation emitted from one radiation source 230a (e.g., a radiation source characterized by a wavelength of approximately 518 nm) will first be considered in reference to FIG. 6. This treatment will simplify the discussion. Emission from two sources of radiation characterized by different wavelengths, described in a separate section below, can then be readily understood.

Although a preferred embodiment utilizes at least two radiation sources, in some implementations a single radiation source may be used.

Figure 6:
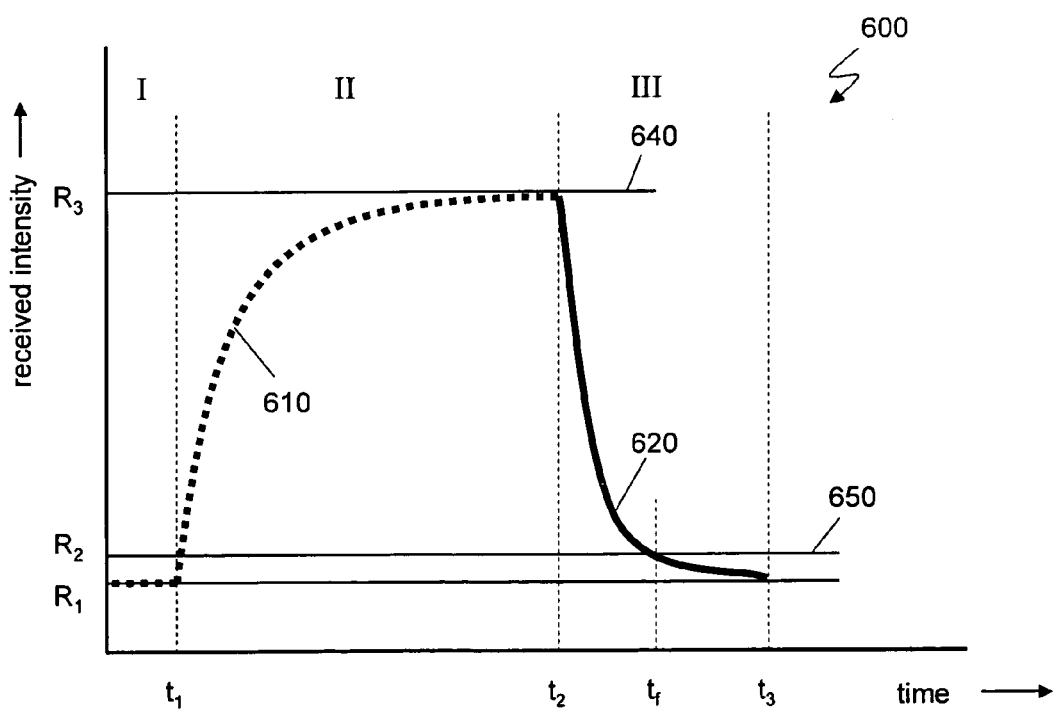
FIG. 6 is a graph illustrating signals representative of blanching of a measurement region and capillary refill within the measurement region.

Operation of apparatus for measuring capillary refill time may be described according to three stages (I, II, III) as illustrated in FIG. 6. A first stage I of operation may comprise identifying a baseline value representative of radiation received from the measurement region when the contact member 220 is not in contact with the measurement region. The second stage II of operation may comprise monitoring the evolution of a signal representative of radiation received from the measurement region when the contact member is pressed against the measurement region. The third stage III of operation may comprise monitoring the evolution of a signal representative of radiation received from the measurement region after the contact member has been released from the measurement region. Calculation of the capillary refill time may be carried out at the conclusion of the third stage, and may be based on data received during the first and third stages of operation. Although operation is described in three stages, the invention should not be limited in this regard. There may be additional or fewer stages of operation.

III A. First Radiation

In a first stage I of operation after powering up the apparatus 100, the controller 120 may provide a signal to the first radiation source 230a to illuminate the measurement region 252 with the first radiation, so that a baseline signal indicated as $R_1$ in FIG. 6 may be established. (Since the graph 600 is considered to be an "ideal" case, the effects of noise and random variables are not considered in this overview of operation. Accordingly, the graph 600 depicts smooth lines.) The controller may receive a plurality of signal values from a detector 235a, sampled at various times, after illumination of the measurement region, and monitor the baseline signal level for a period of time to identify an approximately constant value before initiating a second stage of the measurement. If an approximately constant value is not detected, the controller 120 may provide instructions to the user to adjust the probe assembly.

In a second stage II of operation, the controller may issue instructions for applying the contact member 220 of the measurement module 205 to a measurement region of a patient or subject, so as to momentarily exclude at least a portion of blood from, or momentarily reduce blood flow to, the measurement region. The instructions may comprise visual and/or audio instructions to a user or machine instructions to activate pneumatic pressure or mechanical pressure in the probe 110 that will move the contact member into contact with the measurement region. The contact member 220 of the measurement module 205 may be applied to a measurement region 252 of the patient for a first time period $\Delta T_1$ during the second stage of operation. In reference to FIG. 6 the first time period $\Delta T_1$ is depicted as extending from time $t_1$ to time $t_2$. The controller may provide instructions to the probe to illuminate the measurement region with the first source 230a during the first time period. Additionally, the controller may receive signal values from the detector 235a representative of radiation returned from the measurement region during the first time period.

During the first time period $\Delta T_1$, an amount of blood may be excluded over time from the measurement region by the contact member 220. This may result in a blanching of the tissue in the measurement region. As a result, the amount of the first radiation received from the measurement region may increase with time, as depicted by the dashed rising curve 610 in FIG. 6. Accordingly, radiation levels detected by detector 235a will rise with increasing time, and the controller may receive a plurality of rising signal values from the detector 235a. The signal values may be sampled at various times during the first time interval $\Delta T_1$. The sampled signal values during $\Delta T_1$ will trace out a curve similar to the dashed portion 610 shown in FIG. 6. The controller may be configured to process the signal values and determine whether the values saturate (e.g., become approximately constant) or are near to or in excess of a pre-defined limit 640, as is indicated by the dashed curve near the time $t_2$. When the controller has determined that there is a saturation of signal values or the signal values are near to or in excess of a pre-defined first limit 640, the controller may end the second stage of operation and initiate a third stage.

In some embodiments, the controller may determined that there is a saturation of signal values or the signal values are near to a limit by evaluating a derivative associated with the received signal values, e.g., evaluating derivatives of curve 610 as signal values are received by the controller 120. An evaluation of a first derivative of a curve comprises identifying an instantaneous rate of change or slope of the curve at a selected time. An evaluation of a second derivative of a curve comprises identifying a curvature or degree of linearity of the curve at a selected time. A first and/or second derivative may be taken, and the value of the first and/or second derivative used to determine an end of the second stage of operation. A threshold slope value and/or threshold curvature value may be defined as "trigger conditions" to end the second stage.

Calculations of the derivatives may be based on unaveraged or averaged signal values. For example, a first derivative may be quickly estimated from raw signal values according to the following formula for this simplified overview.

$$\frac{dI}{dt} = \frac{(I_n - I_{n-1})}{(t_n - t_{n-1})} \qquad (1)$$

$I_n$ represents a signal value received at a sampling time $t_n$, and $t_{n-1}$ represents a signal value received at a previous sampling time $t_{n-1}$. (Signal values may be sampled tens, hundreds, or thousands of times during a time period $\Delta T$, so that the index n may be an integer ranging from 1 to thousands.) Alternatively, a first derivative may be quickly estimated from averaged signal values according to the following formula.

$$\frac{dI}{dt} = \frac{(I_n + I_{n-1}) - (I_{n-2} + I_{n-3})}{(t_n + t_{n-1}) - (t_{n-2} + t_{n-3})} \qquad (2)$$

More sophisticated methods of evaluating first and/or second derivatives associated with the received signal values may be used in other embodiments. These methods may use additional data points and interpolation.

In a third stage III of operation, the controller may issue instructions to release the contact member 220 from the measurement region 252. The instructions may comprise visual and/or audio instructions to a user or machine instructions to deactivate pneumatic pressure or mechanical pressure in the probe 110. The controller may provide instructions to the probe to illuminate the measurement region with the first source 230a and receive signal values from the detector 235a during a second time period $\Delta T_2$ during the third stage. In reference to FIG. 6 the second time period $\Delta T_2$ is depicted as extending from time $t_2$ to time $t_3$.

The release of the contact member 220 may be rapid, such that the action of releasing does not substantially alter or impede the capillary refilling process. In some embodiments, the release of the contact member may be less than 1 second, less than 0.5 second in some implementations, and yet less than about 0.25 second in some embodiments. The release of the contact member may be assisted with mechanical (e.g., springs), electromechanical (e.g., solenoid), and/or pneumatic apparatus (e.g., application of vacuum or pressure).

During the second time period $\Delta T_2$, the amount of radiation received from the measurement region may decrease in time as blood returns to the region and absorbs more of the incident radiation from the first radiation source 230a. Accordingly signal values provided to the controller during $\Delta T_2$ may trace out a curve similar to the solid portion 620 of the curve shown in FIG. 6. The controller may be configured to process the received signal values and determine whether the values saturate or are near to or less than a pre-defined second limit 650 or baseline value $R_1$, as is indicated by the solid curve near the time $t_3$. When the controller has determined that there is a saturation of signal values or the signal values are near to or less than a second limit, the controller may end the third stage of operation and process the signal values to determine a capillary refill time. As described above, the controller may evaluate first and/or second derivatives associated with the received signals during the second time period $\Delta T_2$ to determine an end to the third stage.

Capillary refill time may be calculated or estimated using any one of a number of metrics and methods. In a preferred embodiment, a standardized metric will be used so that CRT may be meaningfully compared across populations.

One metric for calculating CRT may be based on a selected signal level. For example, capillary refill time may be defined as the amount of time from the release of compression ($t_2$ in FIG. 6) to a point in time when the received signal value returns to within a selected signal level (e.g., lower limit 650) or a predefined percentage of the baseline value $R_1$. The predefined percentage may be a value between 0% and about 25%, between 0% and about 10%, or between 0% and about 5%. As examples, the capillary refill time may be calculated by determining the amount of time between release of the measurement module 205 at time $t_2$ and a time $t_f$ when the received signal value returns to the lower limit, or in other embodiments to a value of about $(R_1 + 0.05\ R_1)$.

Another metric for calculating CRT may be based on a first and/or second derivative of received signal values. The first and/or second derivatives may be calculated as described above, and compared to respective predefined values. For example, capillary refill time may be defined as the amount of time from the release of compression $t_2$ to a point in time when either or both of the first and second derivatives reaches or falls below respective predefined threshold values for the first derivative and/or the second derivative.

Another metric for calculating CRT may be based on fitting a curve (e.g., a decaying exponential curve, or a multi-parameter theoretical curve) to received signal values. An adjustable parameter of the curve may be a time constant that is altered to obtain a best fit to the received signal values. For example, the following function may be fit to the solid curve 620 of FIG. 6.

$$I(t) = I_o \exp\left(-\frac{(t-t_2)}{\tau}\right) \quad (3)$$

A signal value or average signal value near or at the end of the second stage II may be used for $I_o$, and $\tau$ may be adjusted to obtain a least-squares fit of EQ. 3 to the curve 620. The value of $\tau$ yielding the best fit may be taken as the capillary refill time.

Another method of determining capillary refill time may be based on taking a log of the received signals and determining a slope of a line fit to the resulting data. It will be appreciated that any of the above methods or alternative methods may be used to calculate capillary refill time.

After calculating a value for capillary refill time, the controller 120 may display or provide the result to a user or external device. The controller may also store the value in memory along with a patient identification for later retrieval or transmission to a database of patient information.

In some embodiments and referring again to FIG. 6, the controller may automatically repeat operational stages II and III a selected number of times. Capillary refill times calculated after the conclusion of each repeated stage III may be stored and subsequently averaged before providing an averaged result to a user. Such repetition and averaging may improve measurement confidence and resolution. Alternatively, the stages II and III may be repeated at regularly spaced time intervals, so as to monitor a CRT trend in a patient or subject over an extended period of time, e.g., to track patient recovery or effectiveness of medical intervention.

III B. First and Second Radiation

For the overview of operation described above, only radiation from a first radiation source 230a characterized by a first wavelength was considered and noise sources were ignored. In practice, the inventors have found that noise sources (e.g., patient movement, fluctuations in source power or emission, background radiation) can adversely affect measurement results and render some measurements unreliable. In preferred embodiments, a second radiation source 230b characterized by a second wavelength (e.g., a wavelength of approximately 660 nm) is provided to mitigate the effects of noise in measurements of capillary refill time. The second radiation source 230b may illuminate the measurement region substantially simultaneously with the first radiation source, and provide a reference signal.

When a second radiation source 230b is used, a ratio of signal values associated with the first radiation source received from the measurement region and reference signal values associated with the second radiation source received from the measurement region may be taken. For example, a signal value representative of an amount of intensity received from the measurement region associated with the first radiation source 230a may be divided by, or divided into, a reference signal value obtained at substantially the same time and representative of an amount of intensity received from the measurement region associated with the second radiation source 230b. Taking such a ratio of signal values can appreciably mitigate effects of noise and improve measurement reliability and confidence. An example of noise reduction can be seen in reference to FIG. 8, discussed in further detail below.

In various embodiments, the measurement apparatus 100 includes circuitry at the probe 110 or controller 120, or machine-readable instructions executed by a microprocessor 420, that determines a ratio signal value $R_n$ for each time sampling of detected first radiation signal value $SIG_n$ and detected second radiation reference signal value $REF_n$. $R_n$ may be proportional to a ratio of $SIG_n$ and $REF_n$. For example, $R_n \propto (SIG_n/REF_n)$ or in some embodiments, $R_n \propto (REF_n/SIG_n)$.

In operation, the controller may operate as described above in connection with the first radiation source, wherein ratio signal values are used rather than a signal value representative of the first radiation received from the measurement region. For example, the controller may determine a baseline value in the first stage I based on the ratio signal values. The controller may determine an end to the second stage and third stage based on a saturation of ratio signal values, a level of ratio signal values, or a first derivative and/or second derivative associated with ratio signal values. The calculation of capillary refill time may be also based on ratio signal values.

In some embodiments, measurement results may be improved by normalizing and/or offsetting one or both of the signal value $SIG_n$ and detected second radiation reference signal value $REF_n$ prior to computing a ratio of signal values. Such pre-processing can avoid artifacts that may arise from zero crossings of signals and variations in relative amplitudes.

IV. Methods of Measuring Capillary Refill Time

It will be appreciated that there are various embodiments of methods for measuring capillary refill time associated with measurement apparatus 100 as described above. One embodiment of a method 700 for measuring capillary refill time is depicted in the flow diagram of FIG. 7. Some of the acts shown in FIG. 7 may or may not be included and may be performed in different order in alternative embodiments. Additional steps may be added, and some steps may be deleted. Some of the acts may be executed manually. In some embodiments, all acts may be executed automatically by the controller 120.

According to one embodiment, a method 700 for measuring capillary refill time may comprise an act of establishing 701 a baseline signal value. A baseline signal value may be taken to be a ratio signal value $R_n$, described above, that maintains an approximately constant value for a selected time interval. The selected time interval may be a period of time having a duration between 0 seconds and about 10 seconds, between 0 seconds and about 5 seconds, between 0 seconds and about 2 seconds, and yet between 0 seconds and about 1 second in some embodiments. The act of establishing 701 a baseline signal value may comprise illuminating the measurement region 252 with at least one first radiation source 230a characterized by a first wavelength and at least one second radiation source 230b characterized by a second wavelength. The act of establishing 701 a baseline signal value may comprise receiving, by the controller 120, a first signal representative of radiation from the at least one first radiation source received from the measurement region and detected by at least one first detector 235a, and receiving by the controller a second reference signal representative of radiation from the at least one second radiation source received from the measurement region and detected by at least one second detector 235b.

The act of establishing 701 a baseline signal value may further comprise determining an end, by the controller, to a first stage of operation during which the baseline value is determined. For example, the controller may determine that an approximately constant value of $R_n$ has been maintained for the selected time interval and in response, terminate the first stage of operation. The act of establishing 701 a baseline signal value may further comprise storing, by the controller, the baseline signal value for subsequent reference.

Method 700 may include an act of applying 702 a measurement module 205 of a probe 110 to a measurement region of a patient or subject during a second stage of operation. The act of applying 702 a measurement module may include providing, by the controller 120, visual and/or audio indications to a user to apply the measurement module. The act of applying 702 a measurement module may include providing, by the controller 120, machine instructions to apparatus that cause the application of the measurement module 205 to the measurement region 252.

Method 700 may comprise, during a first period, repeated acts of emitting 704 first radiation from first radiation source 230a, detecting 706 first radiation received from the measurement region, emitting 708 second radiation from second radiation source 230b, detecting 710 second radiation received from the measurement region, and calculating 712 a first ratio of a signal representative of the detected first radiation and a signal representative of the detected second radiation. Any of the acts of emitting radiation may comprise modulating, by the controller, the intensity of the radiation source, or alternatively maintaining a substantially constant intensity. Any of the acts of detecting may comprise modulating a bias on a detector or sampling a sensed signal at discrete times. Any of the acts of detecting may comprise optically filtering radiation received by a detector and/or digitally filtering or averaging signals provided by a detector.

The acts of emitting 704 and detecting 706 first radiation and emitting 708 and detecting 710 second radiation may be carried out at alternate time intervals during the first period (e.g., if a single detector is used), or may be carried out simultaneously during the first period (e.g., if a first detector configured to sense substantially only the first radiation and a second detector configured to sense substantially only the second radiation are used). The repetition of the acts of emitting 704, 708, detecting 706, 710, and calculating 712 may be many times per second, e.g., tens, hundreds, or even thousands of times per second. The act of calculating 712 a first ratio may further comprise storing the calculated value for subsequent retrieval and processing and storing data representative of an approximate time at which signal values used to calculate the first ratio were obtained.

The method 700 may further comprise determining 720 an end to the first period. The end to the first period may be identified by the controller 120 as described above, e.g., by determining a saturation of ratio signal values, by comparing ratio signal values to a first limiting value, by comparing first and/or second derivatives associated with ratio signal values to respective pre-defined first and/or second derivative values. If it is determined that the first period has not ended, the method may return to the acts of emitting 704, 708, detecting 706, 710, and calculating 712. If it is determined that the first period has ended, the method may proceed to an act of releasing 731 the measurement module 205 of the probe 110 from the measurement region.

The act of releasing 731 the measurement module may comprise providing, by the controller 120, visual and/or audio indications to a user to release the measurement module 205 from the measurement region. The act of releasing 731 the measurement module may include providing, by the controller 120, machine instructions to the probe that cause the release of the measurement module 205 from the measurement region 252. In some embodiments, the releasing action may be rapid, e.g., less than one second.

During a second period of operation, the method 700 may include repeated acts of emitting 734 first radiation from first radiation source 230a, detecting 736 first radiation received from the measurement region, emitting 738 second radiation from second radiation source 230b, detecting 740 second radiation received from the measurement region, and calculating 742 a second ratio of a signal representative of the detected first radiation and a signal representative of the detected second radiation. The repeated acts during the second period of operation may be substantially the same as the repeated acts during the first period of operation. The act of calculating 742 the second ratio may further comprise recording the second ratio for subsequent retrieval and processing, and storing data representative of an approximate time at which signal values used to calculate the second ratio were obtained.

The method 700 may further comprise determining 750 an end to the second period. The end to the second period may be determined by the controller 120 as described above, e.g., by determining a saturation of ratio signal values, by comparing ratio signal values to a second limiting value, by comparing first and/or second derivatives associated with ratio signal values to respective pre-defined first and/or second derivative values. If it is determined that the second period has not ended, the method may return to the acts of emitting 734, 738, detecting 736, 740, and calculating 742. If it is determined that the first period has ended, the method may proceed to an act of calculating 760, by the controller 120, a capillary refill time.

The act of calculating 760 capillary refill time may comprise computing, by at least one processor 420, using any one of the techniques described above in connection with calculating a capillary refill time. The act may further comprise displaying the value on display 410 or providing an audio indication to a user and/or storing the calculated value for subsequent retrieval. The value may be stored in association with patient identification data.

Method 700 may further comprise determining 770 whether to repeat a measurement of capillary refill time. The act of determining 770 whether to repeat a measurement may comprise user interaction in some embodiments. For example, the act of determining 770 may comprise providing, by the controller, a query to the user so as to prompt a first user response to repeat the measurement or a second user response to end the measurement. The query may be a visual display and/or audio or tactile prompt.

In some implementations, the act of determining 770 may be executed automatically by the controller. For example, the microprocessor 420 may monitor signal noise or signal variability during a measurement. If the signal noise is within a predefined limit, then the controller may determine that the measurement should not be repeated. If the signal noise exceeds a predefined limit, then the controller may determine that the measurement should be repeated and return to the act of establishing 701 a baseline signal value or the act of applying 702 the measurement module.

In some implementations, the acts of detecting 706, 710, 736, 740 may further comprise storing detected values for subsequent processing. In this regard, the acts of calculating 712, 742 ratios may occur after the respective acts of determining 720, 750 ends to the respective periods. In this regard, the steps of calculating 712, 742 may further comprise pre-processing the stored detected values to normalize and/or offset the values before calculating respective first and second ratios.

In some implementations, the durations of the first period and second period may be predefined. For example, the duration of the first period may be a fixed time value between about 0.1 second and about 4 seconds. The duration of the second period may be a fixed value between about 1 second and about 10 seconds. In such an embodiment, the steps of determining 720, 750 and end to respective time periods may comprise determining whether the fixed time value has expired. In such an embodiment, the acts of calculating 712, 742 ratios may occur after an end to each period or prior to the act of calculating 760 the CRT. In some embodiments, the acts of detecting 706, 710, 736, 740 may further comprise storing detected values for subsequent retrieval and processing.

EXAMPLES

A prototype apparatus for measuring capillary refill time, depicted in FIGS. 5A-5B, was developed by the inventors and trialed in several experiments. Results from the experiments are described in this section. The prototype apparatus included a probe comprising a hand-held measurement module 205 and a hand-held controller 120. The measurement module could be applied manually to a measurement region 252 of a patient, and included high-power LEDs with characteristic wavelengths at approximately 518 nm and approximately 660 nm as the first and second radiation source, respectively. For the prototype apparatus, the LEDs were alternately illuminated multiple times per second, and a single optical detector (TSL230, available from Texas Instruments of Austin, Tex.) was used to detect alternately radiation received from the measurement region for the first and second radiation sources. The longer wavelength source provided a reference signal that was substantially unaffected by the presence or absence of blood in the measurement region. Variations in the reference signal received from the measurement region were representative of variations in probe placement, probe alignment, probe-to-measurement-region distance, and pigmentation of the measurement region. A ratio of the signals received from the measurement region can substantially cancel signal variations due to probe placement, probe alignment, probe-to-measurement-region distance, and pigmentation of the measurement region. The contact member 220 of the probe comprised a rounded acrylic window.

Experiment 1

Measurements of Capillary Refill

For the first experiment, the measurement module was manually pressed against a measurement region of a patient for a first period of time until a detected signal was observed to saturate, and then manually retracted so that there was no pressure of the module on the measurement region. The module was then maintained in a no-pressure state for a second period. Signals received from the measurement region were recorded during each period and ratios calculated. A microcontroller was used in the controller to acquire data, and was interfaced with a computer for subsequent data processing.

In the first experiment, a clinical application was simulated. The contact member 220 of the measurement module 205 was compressed against a measurement region 252 located on the distal thumb. The 518 nm signal detected from the measurement region was observed to increase as the blood flow in the capillaries was decreased by the compression, while the 660 nm detected from the measurement region showed little variation. The results for each detected signal are plotted on the graph 802 of FIG. 8A.

Figure 8A:
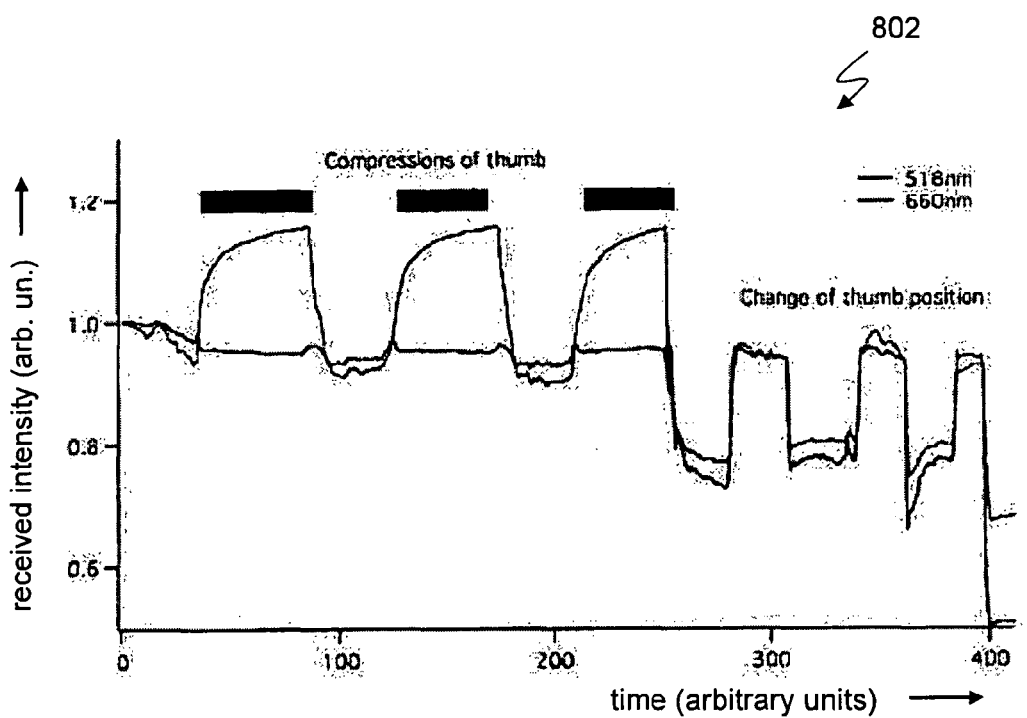
FIGS. 8A and 8B represent measurement results of capillary refill time (left portion of graph) and signal sensitivity to movement of the measurement region (right portion) as obtained using the prototype device of FIG. 6.

The left portion of FIG. 8A shows results for the application of the measurement module to the measurement region and release from the measurement region. The solid bars above the graph indicate where compression of the measurement region occurs. For the right portion of the graph, there was no compression of the measurement region. Instead, the thumb was moved relative to the measurement module, and the resulting signal variations show sensitivity to probe placement.

Figure 8B:
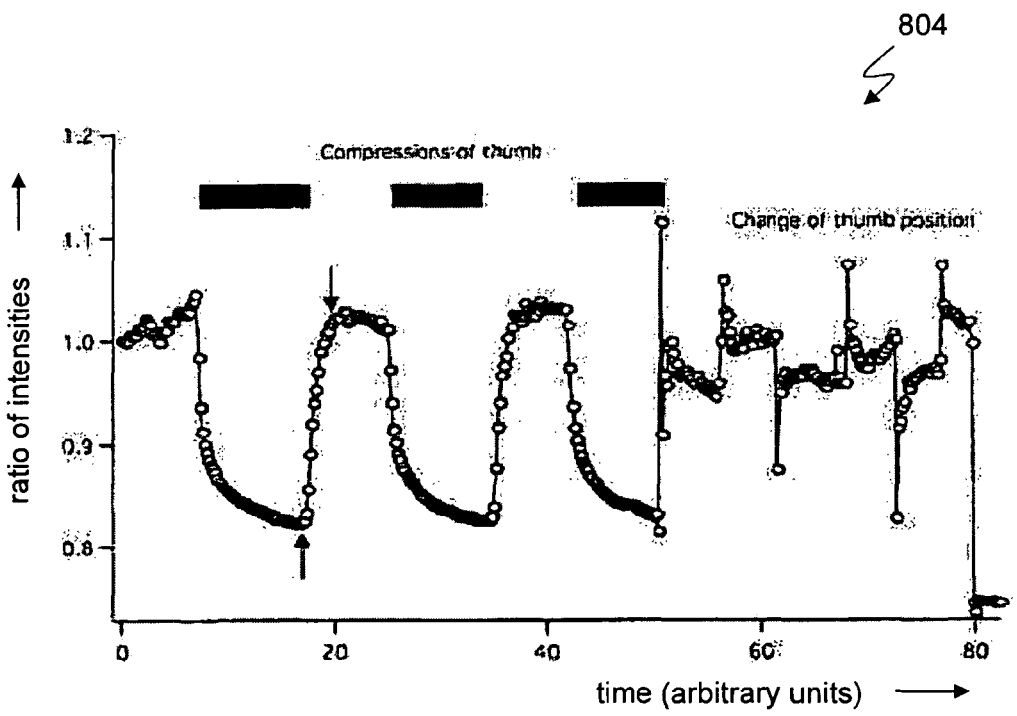

The ratio values of the signals recorded in FIG. 8A are plotted on the graph 804 of FIG. 8B. The ratio values $R_n$ were calculated according to $R_n=(SIG_{n,518}/REF_{n,660})$, which in the present case results in inverted trends compared to the 518 nm signal. The results show a smoothing of the ratio signal resulting from a cancellation of measurement artifacts. The reduction in measurement artifacts can be more clearly seen from the right portion of the graphs where large variations due to thumb movement are suppressed. Digital filtering could improve the ratio signal further.

In this experiment, the microcontroller was programmed to determine a baseline signal before compression and determine an end to the compression time period. The microcontroller would then issue instructions to indicate to the user that the probe may be released from the measurement region. The microcontroller acquired signal values and reference signal values during compression and release. The capillary refill time was calculated to be the amount of time from release of the measurement module to a return of the ratio signal to within about 5% of the baseline value. The arrows indicate the capillary refill time for one of the compression-and-release measurements.

Experiment 2

Measurements of Blood Reflow into a Hand

Figure 9A:
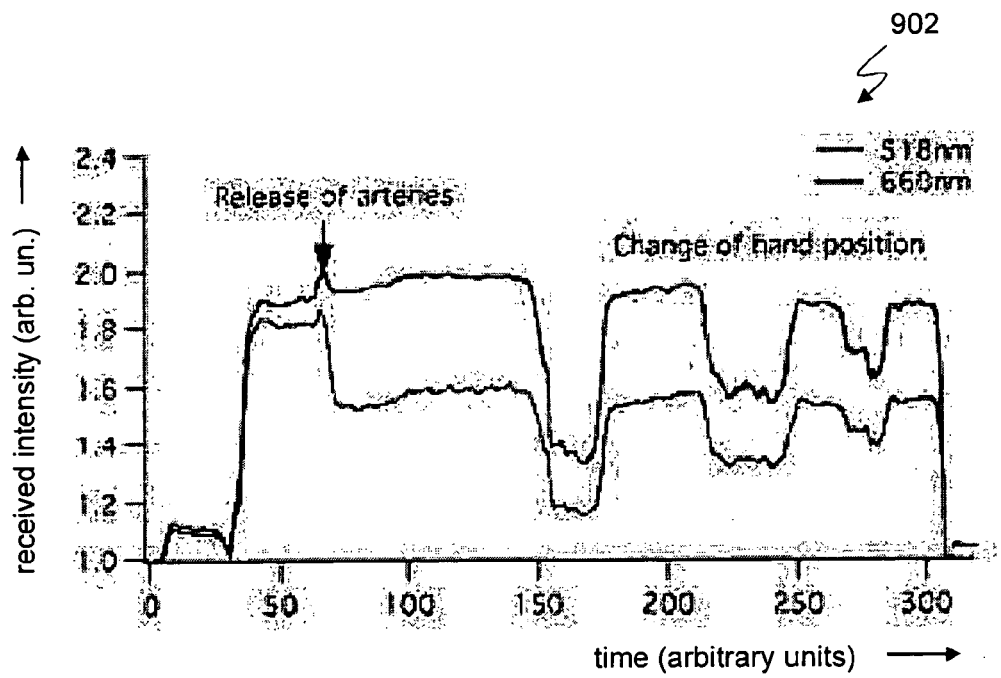
FIGS. 9A and 9B represent measurement results showing the refilling of blood into a hand as obtained using the prototype device of FIG. 6.
Figure 9B:
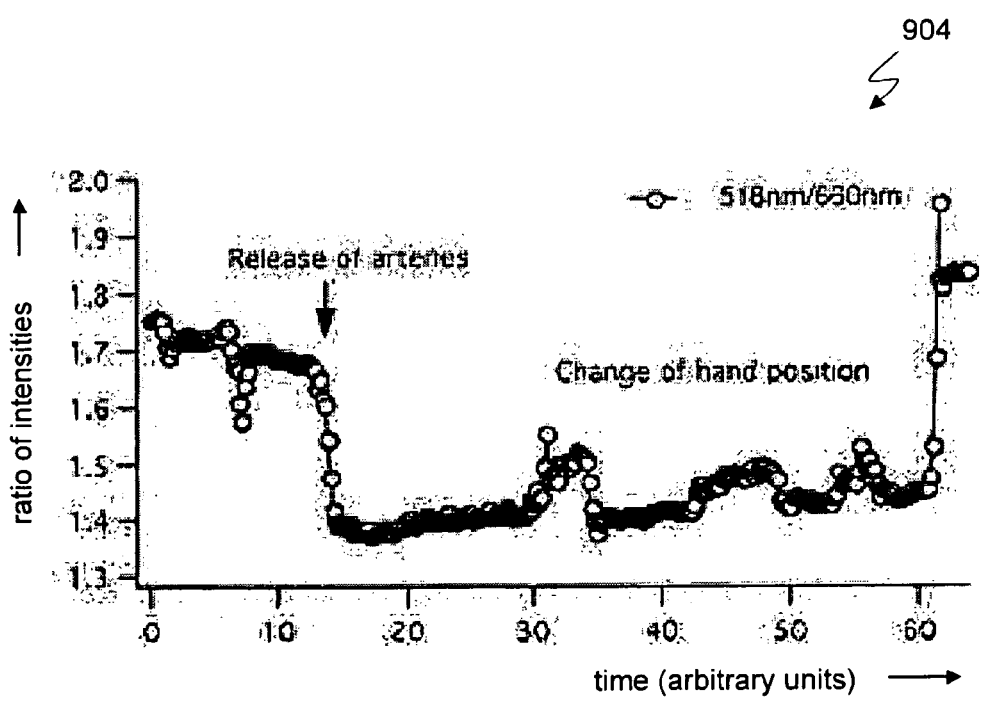

In the second experiment, the prototype apparatus was used to record reflow of blood into a capillary bed in a defined region of tissue on a hand following a modified Allen test. (Cagli, K., et al., "Correlation of modified Allen test with Doppler ultrasonography," Asian Cardiovasc Thorac Ann, Vol. 14, pp. 105-108 (2006)) The probe was placed on the hyperthenar eminence of the hand after occlusion of both the radial and ulnar arteries by direct compression. After removal of compression on the arteries, blood returned to the hand and the reflectances from the measurement region at both 518 nm and 660 nm were recorded. The raw data (see left portion of FIG. 9A) shows a rapid decrease in the detected signal for the 518 nm radiation received from the measurement region, and corresponds to recovery of blood into the hand. There was little change in the detected 660 nm signal during a similar interval of time. The ratio of the signals is plotted in FIG. 9B.

At a later time (right portions of FIGS. 9A-9B) the distance between the measurement module and tissue was changed while the radiation signals received from the measurement region were continually recorded. Both the 518 nm and 660 nm signals were observed to vary responsive to movement of the module with respect to the measurement region. The ratio of signals shown in FIG. 9B suppresses the variations of measurement artifacts and shows that the ratio signal values remain approximately at a baseline value.

Conclusion

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention, e.g., control of the probe 110, processing of signals received from the probe, calculation of capillary refill time (CRT), may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

Terms of degree, "about," "approximately," "substantially," may be used throughout the specification. Such terms of degree may refer to values that are within a selected percentage of or equal to an identified value, e.g., within 30%, within 20%, within 10%, within 5%, within 2%, within 1%, and yet within 0.5% of or equal to an identified value in some embodiments.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. An apparatus for measuring capillary refill time comprising:
at least one source for emitting first radiation characterized by a first wavelength in a range between about 500 nm and about 550 nm, wherein the first radiation is used to detect an amount of blood in a measurement region and wherein the first wavelength is absorbed by an amount of oxyhemoglobin substantially equally as much as the first wavelength is absorbed by the same amount of deoxyhemoglobin, and for emitting second radiation characterized by a second wavelength as a reference wavelength;
at least one detector for detecting the first radiation and the second radiation; and a probe including a convex surface configured to be controllably applied against and released from a measurement region including a capillary bed, wherein the at least one source is configured to radiate the measurement region and the at least one detector is configured to detect the first radiation and the second radiation received from the measurement region.

2. The apparatus of claim 1, wherein the convex surface is configured to be applied against the measurement region to exclude blood from the capillary bed and to be controllably released from the measurement region to allow perfusion of blood into the capillary bed.

3. The apparatus of claim 1 wherein the second radiation is substantially unaffected by the presence or absence of blood in the measurement region and the second wavelength is in a range between about 600 nm and about 750 nm.

4. The apparatus of claim 1, wherein at least a portion of the probe comprising the convex surface is transparent to the first radiation and second radiation.

5. The apparatus of claim 4, wherein the at least one source is configured to emit first and second radiations through the at least a portion of the probe and the at least one detector is configured to detect the first radiation and/or second radiation returned through the at least a portion of the probe.

6. The apparatus of claim 4, wherein the at least a portion of the probe comprising the convex surface is configured to at least partially collimate or at least partially focus the first radiation and/or the second radiation.

7. The apparatus of claim 1, further comprising a controller configured to:
cause the at least one source to emit first and second radiations during at least one first period;
calculate first ratios, for a first plurality of times during the at least one first period, of first signals and second signals from the at least one detector, wherein each one of the first signals is representative of an amount of the first radiation received from the measurement region and each one of the second signals is representative of an amount of the second radiation received from the measurement region at a respective one of the first plurality of times;
identify an end to the at least one first period based on a first trend in the first ratios or a value of one of the first ratios;
cause the at least one source to emit first and second radiations during at least one second period;
calculate second ratios, for a second plurality of times during the at least one second period, of third signals and fourth signals from the at least one detector, wherein each one of the third signals is representative of an amount of the first radiation received from the measurement region and each one of the fourth signals is representative of an amount of the second radiation received from the measurement region at a respective one of the second plurality of times; and
calculate a capillary refill time based on a second trend of the second ratios or a value of one of the second ratios.

8. A method for measuring capillary refill time with the apparatus of claim 1 comprising:
emitting, by a first source of the at least one source, the first radiation characterized by the first wavelength onto a measurement region including a capillary bed;
emitting, by a second source of the at least one source, the second radiation characterized by the second wavelength onto the measurement region;
detecting, by the at least one detector, the first radiation and the second radiation received from the measurement region;
controllably applying and releasing the convex surface of the probe against the measurement region;
calculating a value representative of a ratio of the first radiation and the second radiation received from the measurement region.

9. The method of claim 8, further comprising:
emitting respective radiations from the first source and second source during at least one first period;
calculating first ratios by at least one processor, for a first plurality of times during the at least one first period, of first signals and second signals from the at least one detector, wherein each one of the first signals is representative of an amount of the first radiation received from the measurement region and each one of the second signals is representative of an amount of the second radiation received from the measurement region at a respective one of the first plurality of times;
identifying, by the at least one processor, an end to the at least one first period based on a first trend in the first ratios or a value of one of the first ratios;
emitting respective radiations from the first source and second source during at least one second period;
calculating second ratios by the at least one processor, for a second plurality of times during the at least one second period, of third signals and fourth signals from the at least one detector, wherein each one of the third signals is representative of an amount of the first radiation received from the measurement region and each one of the fourth signals is representative of an amount of the second radiation received from the measurement region at a respective one of the second plurality of times; and
calculating, by the at least one processor, a capillary refill time based on a second trend of the second ratios or a value of one of the second ratios.

10. The method of claim 9, further comprising:
identifying, by the at least one processor, at least one derivative value of the second trend; and
identifying, by the at least one processor, a capillary refill time based on the at least one derivative value.

11. The apparatus of claim 1, wherein the at least one detector comprises a single photodetector arranged to detect the first radiation and the second radiation that are scattered from the measurement region.

12. The apparatus of claim 1, wherein the at least one detector comprises:
at least one first detector including a first radiation filter, the at least one first detector and first radiation filter configured to detect substantially only the first radiation received from the measurement region; and
at least one second detector including a second radiation filter, the at least one second detector and second radiation filter configured to detect substantially only the second radiation received from the measurement region, and
wherein the apparatus is configured to calculate a ratio of the first signal and second signal.

13. The apparatus of claim 1, wherein the first wavelength is in a range between about 500 nm and about 530 nm, and the second wavelength is in a range between about 600 nm and about 750 nm.

14. The apparatus of claim 1, wherein the first wavelength is approximately 518 nm.

15. The apparatus of claim 1, wherein the at least one source and the at least one detector are affixed to the probe.

16. The apparatus of claim 1, further comprising a third source for emitting third radiation characterized by a third wavelength, the third wavelength being in a range between about 900 nm and about 950 nm.

17. The apparatus of claim 1, further comprising a third source for emitting third radiation characterized by a third wavelength, the third wavelength being in a range between about 400 nm and about 500 nm.

18. The apparatus of claim 1, wherein a source of the at least one source is configured to be modulated.

* * * * *